United States Patent
Durst et al.

(10) Patent No.: US 6,358,752 B1
(45) Date of Patent: *Mar. 19, 2002

(54) LIPOSOME-ENHANCED TEST DEVICE AND METHOD

(75) Inventors: Richard Allen Durst, Romulus; Richard A. Montagna, Grand Island; Antje J. Bäumner, Romulus; Sui Ti A. Siebert, Geneva; Geoffrey S. Rule, Aurora, all of NY (US)

(73) Assignees: Cornell Research Foundation, Inc., Ithaca; Innovative Biotechnologies International, Inc., Grand Island, both of NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/315,576

(22) Filed: May 20, 1999

Related U.S. Application Data

(63) Continuation-in-part of application No. 08/722,901, filed on Sep. 27, 1996, now Pat. No. 5,958,791.
(60) Provisional application No. 60/106,122, filed on Oct. 29, 1998, and provisional application No. 60/086,190, filed on May 21, 1998.

(51) Int. Cl.$^7$ .............................................. G01N 33/53
(52) U.S. Cl. ..................... 436/514; 436/518; 436/806; 435/7.1; 435/7.93; 435/7.94; 435/970; 204/194; 204/400; 204/290 R
(58) Field of Search .................. 204/194, 400, 204/290 R; 435/7.1, 7.93, 7.94, 970; 436/518, 806, 514

(56) References Cited

U.S. PATENT DOCUMENTS

| | | |
|---|---|---|
| 4,048,298 A | 9/1977 | Niswender |
| 4,822,566 A | 4/1989 | Newman |
| 4,920,046 A | 4/1990 | McFarland et al. |

(List continued on next page.)

FOREIGN PATENT DOCUMENTS

| | | |
|---|---|---|
| GB | 2 204 398 A | 11/1988 |

OTHER PUBLICATIONS

Rule et al., "Rapid Method for Visual Identification or Specific DNA Sequences Based on DNA–Tagged Liposomes", *Clin. Chem.*, 42(8):1206–1209 (1996).

(List continued on next page.)

*Primary Examiner*—Bao-Thuy L. Nguyen
(74) *Attorney, Agent, or Firm*—Nixon Peabody LLP

(57) ABSTRACT

A test device and method for detecting or quantifying an analyte in a test sample employs an interdigitated electrode array and electroactive marker-encapsulating liposomes for signal generation and detection. The test device includes a contact portion on a first absorbent material, a capture portion either on the first absorbent material, or on a second absorbent material in fluid flow contact with the first absorbent material. The capture portion has a binding material specific for a portion of the analyte bound thereto. The device further includes an electrode array including first and second conductors each having a plurality of fingers, wherein the fingers of the conductors are interdigitated. The electrode array is positioned to induce redox cycling of an electroactive marker released either in or beyond the capture portion, depending upon whether direct (proportional) or indirect (inversely proportional) detection or measurement is desired. In the method of the invention, the test sample is applied to the contact portion, and allowed to migrate along the absorbent material(s) into the capture portion. Either before or after the migration, the test sample is contacted with a conjugate of liposomes and a second binding material for the analyte. To the extent that analyte is present in the sample, the conjugate is bound in the capture portion. By applying a voltage across the conductors, redox cycling of the marker is induced and a current is generated.

28 Claims, 14 Drawing Sheets

U.S. PATENT DOCUMENTS

| | | | |
|---|---|---|---|
| 5,001,048 | A | 3/1991 | Taylor et al. |
| 5,006,473 | A | 4/1991 | Bouma et al. |
| 5,045,285 | A | 9/1991 | Kolesar, Jr. |
| 5,096,629 | A | 3/1992 | Nanba et al. |
| 5,130,257 | A | 7/1992 | Baer et al. |
| 5,141,868 | A | 8/1992 | Shanks et al. |
| 5,200,051 | A | 4/1993 | Cozzette et al. |
| 5,308,775 | A | 5/1994 | Donovan et al. |
| 5,312,762 | A | 5/1994 | Guiseppi-Elie |
| 5,354,692 | A | 10/1994 | Yang et al. |
| 5,384,264 | A | 1/1995 | Chen et al. |
| 5,494,803 | A | 2/1996 | Carbonell et al. |
| 5,532,133 | A | 7/1996 | Barnwell |
| 5,591,645 | A | 1/1997 | Rosenstein |
| 5,712,170 | A | 1/1998 | Kouvonen et al. |
| 5,753,519 | A | 5/1998 | Durst et al. |
| 5,756,362 | A | 5/1998 | Durst et al. |
| 5,776,487 | A | 7/1998 | Wilson et al. |
| 5,789,154 | A | 8/1998 | Durst et al. |
| 5,958,791 | A * | 9/1999 | Roberts et al. |
| 6,159,745 | A * | 12/2000 | Roberts et al. |

OTHER PUBLICATIONS

Rule et al., "Characteristics of DNA–Tagged Liposomes Allowing Their Use in Capillary–Migration, Sandwich–Hybridization Assays", *Anal. Biochem.*, 244:260269 (1997).

Niwa et al. "Electrochemical Behavior of Reversible Redox Species at Interdigitated Array Electrodes with Different Geometries: Consideration of Rodox Cycling and Collection Efficiency", *Anal. Chem.*, 62:447–452 (1990).

Niwa et al., "Small–Volume Voltammetric Detection of 4–Aminophenol with Interdigitated Array Electrodes and Its Application to Electrochemical Enzyme Immunoassay", *Anal. Chem.*, 65:1559–1563 (1993).

Durst et al., "Development of Liposome–Enhanced Immuno–Biosensing Devices for Field Measurements of Toxic Sybstances", $2^{nd}$ Bioelectroanalytical Symposium, 15–32 (1992).

* cited by examiner

LIPOSOME-ENHANCED TEST DEVICE AND METHOD

This application claims the benefit of U.S. Provisional Patent application Ser. No. 60/086,190, filed May 21, 1998, and U.S. Provisional Patent application Ser. No. 60/106,122, filed Oct. 29, 1998, and is a continuation-in-part of U.S. patent application Ser. No. 08/722,901, filed Sep. 27, 1996 now U.S. Pat. No. 5,958,791.

FIELD OF THE INVENTION

The present invention relates to a method for detecting or quantifying an analyte, and a test device used in the method. More particularly, the invention relates to a biosensor test device and method employing marker-loaded liposomes and electrochemical detection for signal amplification and quantitation.

BACKGROUND OF THE INVENTION

There exist a variety of techniques useful for detecting and/or measuring the concentration of an analyte in a test sample. Such techniques include immunoassays, as described in U.S. Pat. Nos. 5,789,154; 5,756,362; and 5,753,519, each of which is hereby incorporated by reference.

Immunoassays employing electrochemical detection are described in U.S. Pat. No. 4,822,566 to Newman, and Niwa, O.; Xu, Y.; Halsall, H. B.; and Heineman, W. R. Anal Chem. 1993, 65, 1559–1563 ("Niwa"). Newman describes a multilayer immunoassay device which relies on the movement of biological species into or out of a biological binding layer in the course of biospecific binding reactions. This movement changes the dielectric constant of the fluid medium containing the analyte, resulting in capacitance changes detected by a sensor. A capacitor comprised of an array of interdigitated copper and gold fingers (2 mil wide, 0.5 mil high, separated by 3 mil spaces) formed by photolithographic etching techniques is disclosed. Niwa describes an electrochemical enzyme immunoassay which employs an interdigitated array microelectrode cell to detect 4-aminophenol (PAP), produced during enzyme immunoassay of mouse IgG. The gold interdigitated array consisted of 50 pair of 3 or 5 $\mu$m wide microbands, spaced 2 $\mu$m apart. Silver-plated and unplated gold square electrodes were used as reference and auxiliary electrodes, respectively. The assay was conducted in microwells.

The devices and techniques in Newman and Niwa, however, are relatively complex. For example, the enzyme immunoassay described in Niwa is carried out through multiple steps to completion on an immunowell device, and the reaction solution is then transferred to a separate electrochemical detection device.

Nucleic acid detection methods are potentially useful for detecting and measuring the presence of organisms, such as pathogens in food and water supplies. Southern, northern, dot blotting, reverse dot blotting, and electrophoresis are the traditional methods for isolating and visualizing specific sequences of nucleic acids. Each has advantages and disadvantages. For example, gel electrophoresis, often performed using ethidium bromide staining, is a relatively simple method for gaining fragment length information for DNA duplexes. This technique provides no information on nucleotide sequence of the fragments, however, and ethidium bromide is considered very toxic, although safer stains have been developed recently.

If, in addition to length information, there is a desire to determine the presence of specific nucleotide sequences, either Southern blotting, for DNA, or northern blotting, for RNA, may be chosen. These procedures first separate the nucleic acids on a gel and subsequently transfer them to a membrane filter where they are affixed either by baking or UV irradiation. The membrane is typically treated with a pre-hybridization solution, to reduce non-specific binding, before transfer to a solution of reporter probe. Hybridization then takes place between the probe and any sequences to which it is complementary. The initial hybridization is typically carried out under conditions of relatively low stringency, or selectivity, followed by washes of increasing stringency to eliminate non-specifically bound probe and improve the signal-to-noise ratio.

Originally, probes were often labeled with $^{32}$P which was detected by exposure of the membrane to photographic film. Today, however, many researchers are making use of non-isotopic reporter probes. These blotting procedures require more time and effort than simple gel electrophoresis, particularly when low levels of nucleic acid are present.

Dot, or slot, blotting are essentially equivalent methods which provide sequence homology information only. No separation of nucleic acid sequences is performed prior to hybridization thus saving considerable time. Typically, the entire DNA, or RNA, composition of the sample being evaluated is attached to a nylon, or nitrocellulose, membrane to form a small "dot" of the nucleic acid mixture. The membrane is then probed in a fashion similar to that described for Southern and northern blotting. The technique is simpler than Southern and northern blotting but can give rise to non-specific binding of the probe thus reducing sensitivity. Probes can be labeled with 32P, biotin, various haptens, or enzymes such as horseradish peroxidase and alkaline phosphatase to produce a colored spot on the membrane in the presence of appropriate substrate.

In the reverse dot blot technique, an oligonucleotide capture probe is immobilized on a membrane while the target is kept in solution. In this scheme the target must also bear the reporter entity, usually by indirect registration. An advantage of this strategy is that multiple capture probes can be immobilized on the same membrane so that several target sequences can be determined simultaneously.

There are a wide variety of DNA and RNA detection schemes in the literature, many of which are available as commercial kits. Nucleic acid detection schemes have seen the same trends in assay design as immunoassays, with efforts directed towards simpler, more rapid, and automatable detection schemes.

It is useful to categorize assays based on the fashion in which the signal is produced and detected. Vener et al. (1991) Anal. Biochem. 198, 308–11, classified hybridization probe use into two categories: direct registration and indirect registration. Direct registration, not to be confused with direct hybridization, is defined as the use of a reporter probe which itself is capable of producing a detectable signal. This may be by labeling with a radioisotope, fluorescent tag, enzyme, or sol particle. Most of the initial work done with nucleic acid hybridization made use of direct registration with $^{32}$P labelled probes.

An example of this type of assay is that reported by Pollard-Knight et al., (1990) Anal. Biochem. 185, 84–9. These researchers used probes labelled directly with horseradish peroxidase in an enhanced chemiluminescence detection scheme. Single-copy sequences of human genomic DNA were immobilized on nitrocellulose membranes, by Southern blotting, and targeted with enzyme-labelled probes of lengths between 50 and 3571 bases. One enzyme existed for every 50–100 bases of the probe so that better sensitivity was obtained with longer probe lengths. The use of a special blue sensitive film, along with a commercial enzyme substrate, allowed the detection of one amol of several different target sequences.

In indirect registration the probe itself does not bear the signal producing, or reporter entity, rather it bears a ligand such as biotin, fluorescein, digoxigenin, or, in some cases, a non-complimentary nucleotide sequence, which is then specifically recognized by a separate biomolecule or receptor. The latter then either generates or bears the signal producing molecules. This type of assay is very commonly used as a non-isotopic replacement for $^{32}P$ labeling and is available as commercial kits produced by Amersham International (Arlington Heights, Ill.) and Boehringer Mannheim (Indianapolis, Ind.).

The water-borne pathogen *Cryptosporidium parvum* illustrates the need for efficient and inexpensive nucleic acid detection methods. *Cryptosporidium parvum* is found in water supplies and food. Its life cycle includes oocysts that can be difficult to control by drinking water treatment processes such as chemical disinfection and filtration. The ingestion of oocysts can cause serious illness. Table 1 shows a number of documented water-borne outbreaks of Cryptosporidiosis in recent history.

TABLE 1

| LOCATION OF OUTBREAK (DATE) | NUMBER EXPOSED | NUMBER INFECTED |
| --- | --- | --- |
| Braun Station, TX (1984) | 5,900 | 2,006 |
| Carrolton, GA (1987) | 32,400 | 12,960 |
| Swindon, UK (1989) | 741,092 | 516 |
| Jackson, OR (1992) | 160,000 | 15,000 |
| Milwaukee, WS (1993) | 1,600,000 | 403,000 |
| Las Vegas, NV (1994) | Unknown | 120+ |
| Georgia, water park (1995) | Unknown | 5,449 |

These outbreaks and the difficulty of eliminating Cryptosporidium oocysts from water supplies by conventional water treatment methods demonstrate the need for efficient and inexpensive organism detection methods. Methods for the detection of oocysts have been proposed but they are plagued by poor recovery efficiencies, and seldom provide information regarding the viability of the oocysts that are found in the samples. They also share the deficiencies of existing methods for detecting organisms generally, such as cell culture, agar plate testing, tissue culture, and traditional immunoassay methods, which are laborious, time consuming, and expensive.

In view of the deficiencies and complexities of prior techniques for use as rapid, reliable, and simple assays, the need remains for technology which will accurately detect and determine analytes such as environmental and food contaminants, including pathogenic organisms.

SUMMARY OF THE INVENTION

The present invention provides a method and device for detecting or quantifying an analyte in a test sample employing an electrochemical signal production and amplification system. The test device includes a first absorbent material having a contact portion for receipt of the test sample and other assay components. It further includes a capture portion either on said first absorbent material, or on a second absorbent material in fluid flow contact with said first absorbent material. The capture portion has a first binding material bound to the capture portion.

The test device further includes an electrode array having a first conductor and a second conductor. Each conductor comprises a plurality of fingers, and the fingers of the first conductor are interdigitated with the fingers of the second conductor. The electrode array is positioned to induce redox cycling of an electroactive marker released in the capture portion.

The test device is employed in the method of the invention. In the method, the test sample is applied to the contact portion. Either before or after the application of the test sample, it is contacted and with a conjugate of electroactive marker-encapsulating liposomes and a second binding material. The second binding material is selected to bind with a portion of the analyte. The first binding material is selected to bind with a portion of the analyte other than the portion for which the second binding material is selected. The test sample and conjugate are incubated for a time sufficient to permit reaction between any analyte present in the sample and the second binding material.

The test sample is allowed to migrate from the contact portion toward and then into the capture portion. A voltage sufficient to induce redox cycling of the electroactive marker contained in the liposomes is applied across the conductors. After the test sample and the conjugate are incubated, liposomes bound in the capture portion are lysed to release the marker, which undergoes redox cycling as the result of the voltage applied across the conductors, causing current to flow between said first and second conductors. The presence or the amount of the resulting current is detected and correlated with the presence or amount, respectively, of the analyte in the test sample. In this embodiment, the magnitude of the current released from liposomes bound in the capture portion is directly proportional to the amount of analyte in the test sample.

In another embodiment of the invention, the electrode array is positioned to induce redox cycling of electroactive marker released from liposomes which migrate out of the capture portion. Thus, the presence or amount of the current generated by liposomes which are not bound in the capture portion is detected or measured. In this embodiment, the magnitude of the current generated is inversely proportional to the amount of analyte in the sample.

The device and method of the invention can be used directly in the field. The device is used only once, and, therefore, is free from residual environmental contaminants other than what may be present in the sample to be measured. Samples can be assayed within minutes after collection, with the results immediately available on-site. In addition, the device and method of the invention are less complex than many of the prior materials and methods. The ability to deliver quantitative results without additional steps for spectrophotometric or fluorimetric analysis, is an advantage of the present electrochemical device and method over devices and methods that employ dyes and fluorescent materials as markers.

In addition, electroactive marker-loaded liposomes as used in the device and method of the invention provide a highly sensitive, rapid or even instantaneous signal production/amplification system. Furthermore, the amount of marker measured in the electrochemical measurement portion of the absorbent material of the test device is directly proportional to the analyte concentration in the sample. This feature of the invention provides a particular advantage over prior test devices, nucleic acid detection assays, and immunoassays, providing an intuitive correlation between signal strength and analyte concentration. Electrochemical detection offers greater sensitivity than colorimetric determination and is comparable to fluorimetry or chemiluminescence. In addition, the present invention provides quantitative results that can be obtained directly from the electroanalyzer or other detection instrumentation to which the test device is connected, without the need to transfer the device to a separate optical measurement device. Also, electrochemical detection allows for testing in solutions or mixtures that are highly colored or include particulate matter, and which, therefore, would interfere with optical detection.

Interdigitated electrode arrays are particularly suitable for test strip analysis due to their planar configuration and their inherent sensitivity for electrochemical measurements. Microelectrodes fabricated in an interdigitated array have inherent advantages in signal detection over more conventional electrode configurations. These advantages can only be realized with electrodes of very small dimensions due to the theoretical relationships between electrode geometry and ionic diffusion. Scaling down the size of an individual electrode has the advantage of increasing the rate of mass transport, increasing the signal-to-noise (faradaic/charging current) ratio, and decreasing ohmic signal losses, as described in M. Fleischmann, S. Pons, D. R. Rolison, P. P. Schmidt, Eds. *Ultramicroelectrodes* (Datatech Systems, Inc., Morganton, N.C. 1987), which is hereby incorporated by reference. Advantages of microelectrodes are also described in J. O. Howell, Voltammetric Microelectrodes, Bioanalytical Systems, Inc., West Lafayette Ind. 47906, hereby incorporated by reference.

Advantages of fabricating small electrodes in interdigitated arrays go even further by allowing redox cycling of ions back and forth between anode(s) and cathode(s). See O. Niwa, Y. Xu, B. H. Halsall, W. R. Heineman, Anal. Chem. 65, 1559–1563 (1993) and O. Niwa, H. Tabei, Anal. Chem. 66, 285–289 (1994), each of which is hereby incorporated by reference. This generates much larger currents for detection and allows for the use of extremely small sample volumes. By using a dual potentiostat and a four-electrode system with an interdigitated array, it is possible to almost completely eliminate charging current. This results in a greater signal-to-noise ratio and allows for the use of extremely high scan rates. See O. Niwa, M. Morita, H. Tabei, Anal. Chem. 62, 447–452 (1990) and C. Chidsay, B. J. Feldman, C. Lundgren, R. W. Murray, Anal. Chem. 58, 601–607 (1986), which are hereby incorporated by reference. Furthermore, the sophisticated electronics needed to detect the very small currents associated with individual microelectrode filaments are not necessary due to the summation of current from the large array of microelectrodes.

BRIEF DESCRIPTION OF THE DRAWINGS

FIG. 2b is an exploded view of the test device shown in FIG. 2a.

FIG. 3b is an enlarged view of a portion of the electrode array shown in FIG. 3a.

DETAILED DESCRIPTION OF THE INVENTION

Figure 1:
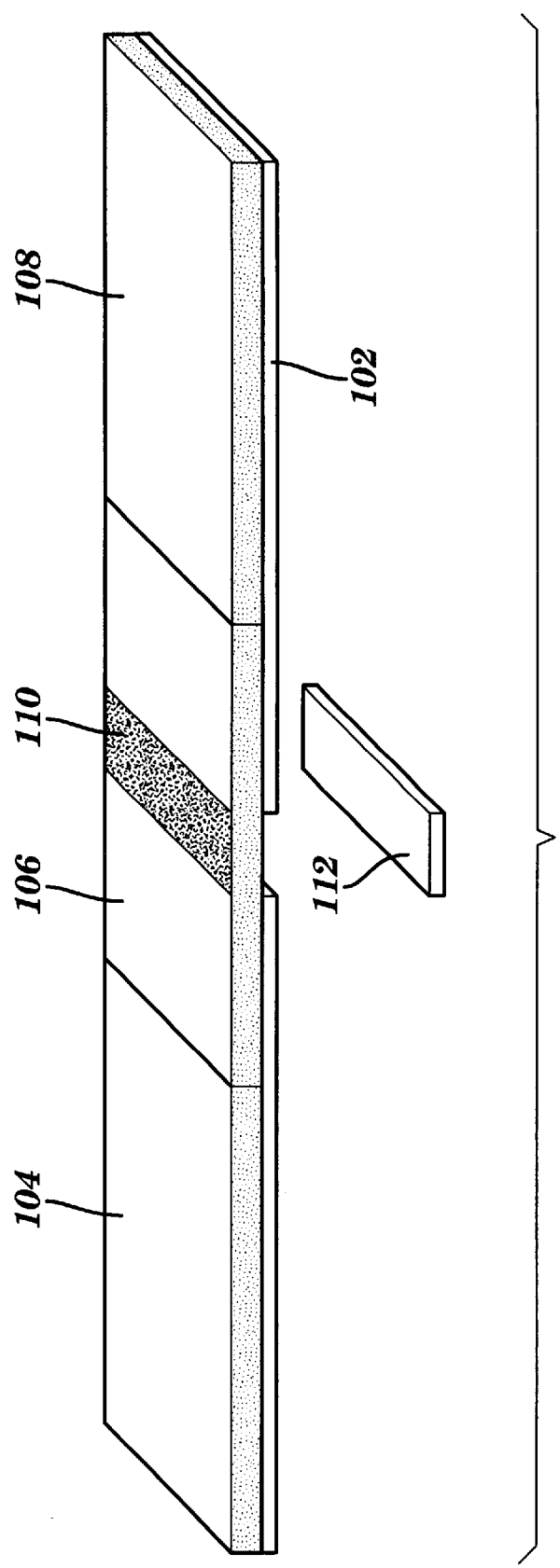
FIG. 1 is a schematic of a test device in accordance with the invention.

The method of the invention employs two binding materials for the target analyte—one conjugated to marker-encapsulating liposomes, the other immobilized on a portion of an absorbent material. The two binding materials bind to different portions of the analyte. An excess of both the liposome conjugate and the immobilized binding material are employed. Thus, to the extent that the analyte is present in the test sample, the marker-loaded liposomes become bound to the absorbent material via the analyte. Thus, the test device and method of the invention rely on the "sandwich" formed by the first binding material (immobilized on the absorbent material), the analyte, and the second binding material (conjugated to the marker-loaded liposomes).

The invention encompasses both direct and indirect detection/measurement methods. In the former, the presence or amount of the marker bound in the immobilization, or "capture" portion of the test device is detected. In this embodiment, the amount of marker bound in the capture portion is directly proportional to the amount of analyte in the test sample. The indirect detection embodiment involves detecting or measuring the marker released from liposome conjugate which migrates beyond the capture portion, which is indirectly proportional to the amount of analyte in the test sample.

By "analyte" is meant the compound or composition to be measured or detected. It is capable of binding to the first and second binding materials. A preferred analyte is a nucleic acid molecule.

By "binding material" is meant a bioreceptor molecule such as an immunoglobulin or derivative or fragment thereof having an area on the surface or in a cavity which specifically binds to and is thereby defined as complementary with a particular spatial and polar organization of another molecule—in this case, the analyte. Alternatively, when the target analyte is a nucleic acid molecule, the first and second binding materials are nucleic acid molecules selected to hybridize with separate portions of the target nucleic acid molecule.

Antibody binding materials can be monoclonal or polyclonal and can be prepared by techniques that are well known in the art such as immunization of a host and collection of sera or hybrid cell line technology. The binding material may also be any naturally occurring or synthetic compound that specifically binds the analyte of interest.

As is discussed in greater detail below, the method of the invention employs a conjugate of marker-encapsulating liposomes and a second binding material. The second binding material may be conjugated to the liposome surface. The second binding material must be bound to the liposomes so as to present a portion of the second binding material that may be recognized by the analyte.

Suitable conjugation methods are discussed in U.S. Pat. Nos. 5,789,154; 5,756,362; and 5,753,519. For example, the liposome surface may be activated with thiol groups and coupled to a maleimide group on the second binding material. Or, conversely, maleimide-activated liposomes and thiol group-activated binding material may be employed.

The first and second binding materials are selected to bind specifically to separate portions of the analyte. For example, when the analyte is a nucleic acid sequence, it is necessary to choose probes for separate portions of the target nucleic acid sequence. Techniques for designing such probes are well-known. Probes suitable for the practice of the present invention must be complementary to the target analyte sequence, i.e., capable of hybridizing to the target, and should be highly specific for the target analyte. The probes are preferably between 17 and 25 nucleotides long, to provide the requisite specificity while avoiding unduly long hybridization times and minimizing the potential for formation of secondary structures under the assay conditions. In addition, the first and second binding materials (capture and reporter probes) should not be capable of hybridizing with one another. Techniques for identifying probes suitable for the practice of the invention are described in J. Sambrook, E. F. Firtsch, and T. Maniatis, "Molecular Cloning: A Laboratory Manual" (Cold Spring Harbor Laboratory Press 1989), which is hereby incorporated by reference. A software program known as "Lasergene", available from DNASTAR, may optionally be used.

In general, to design an assay, the target nucleic acid is extracted from a sample, and then amplified by one of a variety of known amplification techniques. Such amplification techniques include polymerase chain reaction, ligase chain reaction, and Nucleic Acid Sequence Based Amplification (NASBA). See T. Kievits et al., "NASBA isothermal enzymatic in vitro nucleic acid amplification optimized for the diagnosis of HIV-1 infection" Journal of Virological Methods, 35, (1991) 273–286, which is hereby incorporated by reference. NASBA, marketed by Organon-Teknika, is a preferred amplification technique when information regarding the presence or concentration of viable organisms in a sample.

As discussed further below, the test sample known to or suspected of containing the analyte can be combined with the conjugate to form a mixture, which may be a solution, suspension, dispersion, or other mixture. Alternatively, the test sample and the conjugate may be applied separately to the first absorbent material, for example, by spotting each onto the absorbent material in the same or separate locations.

By "absorbent material" is meant a porous material having a pore size of from 0.05 $\mu$m to 50 $\mu$m, preferably from 0.45 $\mu$m to 5 $\mu$m, which is susceptible to traversal by an aqueous medium in response to capillary force. Such materials may be natural polymeric materials, particularly cellulosic materials, such as fiber-containing papers, e.g., filter paper, chromatography paper, etc.; synthetic or modified naturally occurring polymers, such as nitrocellulose, cellulose acetate, poly(vinyl chloride), polyacrylamide, cross linked dextran, agarose, polyacrylate, nylon, activated nylon, polysulfone base modified, etc.; either used by themselves or in conjunction with a support, as described below. Nitrocellulose is a preferred absorbent material for the absorbent pad(s) comprising the contact and capture portions of the test device.

The absorbent materials may be polyfunctional or be capable of being polyfunctionalized to permit immobilization of the second binding material.

The absorbent materials employed in the test device and method of the invention are generally a cellulose ester with nitrocellulose giving exceptionally good results. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such materials, which are formed from cellulose esterified with nitric acid alone, or a mixture of nitric acid and another acid such as acetic acid, are often referred to as nitrocellulose paper.

Although nitrocellulose is a preferred material for producing the test device, it is to be understood that other materials having a surface area sufficient for supporting the agents to be immobilized thereon in a concentration as hereinbelow described may also be employed for producing such test devices.

As described herein, the test device includes one or more absorbent materials. Regardless of the number of absorbent pads or materials employed, it is important that at least that portion of the test strip comprising and between the conjugate application and capture portions be made of a non-liposome lysing material. The material on which the first binding material is immobilized must be capable of supporting the immobilization, and the material(s) must allow liquid migration (lateral flow).

Absorbent materials having high surface areas (such as nitrocellulose) are particularly preferred for some applications in that the first binding material and, if desired, the liposome conjugate, may be supported on such materials in high concentrations. It is to be understood, however, that the concentrations of binding material and liposome conjugate which are actually used are dependent in part on the binding affinity of the first and second binding materials. Accordingly, the scope of the invention is not limited to a particular concentration of binding material on the absorbent material.

Application of the binding material and, if desired, the liposome conjugate to the absorbent material may be accomplished by well-known techniques, for example, by spraying or spotting solutions of these components onto the absorbent material.

The first binding material and/or liposome conjugate can be bound to the absorbent material by covalent bonding. For example, the material to be bound can be applied directly to the absorbent material, and then bonded thereto via ultraviolet radiation. Alternatively, materials can be adsorbed onto the absorbent material, as long as the binding of the first binding material to the absorbent material is non-diffusive. This will involve contacting the absorbent material with a solution containing the material to be bound to the material and allowing the material to dry. In general, this procedure will be useful only where the absorbent material is relatively hydrophobic or has a high surface charge, and subsequent treatment with proteins, detergents, polysaccharides, or other materials capable of blocking nonspecific binding sites will be required.

The first binding material is preferably indirectly bound to the absorbent material in the capture portion of the device. For example, the first binding material is preferably labeled with a tag, for example, biotin, and a ligand that specifically binds the tag, for example, streptavidin or anti-biotin antibody, is applied to the absorbent material in the capture portion. Other agents suitable for immobilizing the first binding material in the capture portion include avidin, anti-fluorescein, anti-digoxin, anti-dinitrophenyl (DNP).

Before or after application of the binding material and, optionally, the liposome conjugate, to the appropriate portion(s) on the absorbent material(s), the residual nonspecific binding capacity of the absorbent material(s) can be, and preferably is, saturated or blocked with one or more types of proteins or other compounds such as polyvinylpyrrolidone, polyvinylalcohol, other suitable polymeric blocking agents etc., which do not specifically bind the materials to be employed in the assay. Blocking is generally carried out after the binding material and liposome conjugate are applied to the strip, but it may be possible to block the strip before these components are applied depending on the method of application, the particular blocking agent and absorbent material employed. Thus, for example, the residual binding capacity of the substrate may be blocked so as to prevent nonspecific binding by the use of bovine serum albumin, as described in Towbin, et al., *Proc. Nat'l. Acad. Sci.*, 76 (1979) 4350, which is hereby incorporated by reference. The techniques for preventing nonspecific binding are generally known in the art, and such techniques are also generally applicable to preventing nonspecific binding in the assay of the present invention. Examples of particularly suitable techniques for blocking with polyvinylpyrrolidone and polyvinylalcohol are described, for example, Bartles, et al. *Anal. Biochem.*, 140 (1984) 784, and in British Patent Specification GB 2204398 A, respectively, which are hereby incorporated by reference. Alternatively, one or more blocking agents can be incorporated into the buffer solution used to wash or carry test components along the absorbent material(s).

In conjunction with a blocking agent or agents, a surfactant may be applied to the absorbent material in a concentration sufficient to promote homogeneous flow of the test solution across the test device, to facilitate migration of the liposome conjugate without lysis of the liposomes. Suitable surfactants include Brij™ (polyoxyethylene ether), Tween 20™ (polyoxyethylenesorbitan monolaurate), Triton X-100™ (t-octylphenoxypolyethoxyethanol), sodium dodecylsulfate, n-octyl- -D-glucopyranoside, Span 20™, Nonindet P-40, Chapso™, Turgitol™ and sodium dioxycholate. The concentration of the surfactant(s) employed in a blocking solution will depend, in part, upon the liposome composition. In general, surfactants may be incorporated in a concentration of from about 0 to about 0.01 volume percent of the blocking solution, preferably from about 0.001 to about 0.005 volume percent of the blocking solution. It is important that the concentration of surfactant applied to the absorbent material be controlled, as premature lysis of the liposomes may occur if the surfactant concentration is too high. Tween 20™ is a preferred surfactant for use in a blocking solution.

The blocking agents block nonspecific binding sites on the absorbent material. The blocking agents are selected from the group consisting of proteinaceous blocking reagents capable of inhibiting binding of molecules having a molecular weight of greater than about 1000 with said absorbent material and polymer blocking reagents capable of inhibiting binding of molecules having a molecular weight of less than about 1000 with said absorbent material. The proteinaceous blocking reagent may be selected from the group consisting of gelatin, non-fat dry milk, bovine serum albumin, keyhold limpet hemocyanin, and casein. The polymer blocking reagent may be selected from the group consisting of polyvinylpyrrolidone and polyvinylalcohol, and the surfactant may be selected from the group consisting of polyoxyethylene ethers, polyoxyethylenesorbitan monolaurate, t-octylphenoxypolyethoxyethanol, and sodium dodecylsulfate, octylglucopyranoside, and sodium dioxycholate.

The test device preferably comprises two or three absorbent pads, laid end-to-end, as discussed more fully below. In the two pad embodiment, the first pad includes both the contact portion and the capture portion, which is preferably begins at or beyond about half-way along the strip, to allow sufficient space on the pad in front of the capture zone for reaction or hybridization of the target with the second binding material carried on the liposomes. A second pad may be employed as a wicking pad, as discussed more fully below, to pull excess reagents out of the first absorbent pad. If three pads are employed, the capture portion is preferably located on the center pad, most preferably at or near the center of the pad. In this embodiment, the wicking pad is the third pad, but an additional pad or pads could be used as wicking pads beyond a third pad.

The test device and method of the invention may alternatively comprise only one pad, as for example, when the sample volume is small. In such a case, it is necessary that the absorbent material have sufficient area beyond the capture portion to absorb sufficient volume of test reagents to permit completion of the reactions or hybridizations on which the assay is based, as discussed more fully below, and, in the case of the indirect measurement embodiment disclosed herein provide space for a sufficient separation between the capture portion and the portion at which the released electroactive marker is measured or detected.

The absorbent material can be a single structure such as a sheet cut into strips. The absorbent materials can be mounted on a support material, described more fully below. On the other hand, the absorbent materials may provide their own support. In one embodiment of the invention, the test device includes a strip of particulate material bound to a support or solid surface such as found, for example, in thin-layer chromatography. The absorbent material can be a sheet having lanes thereon, or be a uniform sheet capable of division into separate lanes by physical removal of the absorbent material from the support to induce lane formation, wherein a separate assay can be performed in each lane as shown copending U.S. patent application Ser. No. 08/722,901, which is hereby incorporated by reference. The absorbent materials can be of a variety of shapes, including rectangular, circular, oval, trigonal, or the like, provided that there is at least one direction of traversal of a test mixture by capillary migration. Other directions of traversal may occur such as in an oval or circular piece contacted in the center with the test mixture. However, the main consideration is that there be one direction of flow from the contact portion through the capture portion. In this discussion, strips of absorbent material are described by way of illustration and not limitation.

The conjugate can be introduced into the device and method in a variety of ways. It is preferably combined with the test sample and may be incubated for a period of time to allow reaction or hybridization to occur between any analyte present in the sample and the second binding material on the conjugate. Where the analyte is a nucleic acid molecule, the mixture is preferably incubated at elevated temperature, i.e., from about 30° C. to 50° C., preferably from about 40° C. to 44° C., for about 3 to 30 minutes.

Alternatively, the liposome-second binding material conjugate can be introduced onto the absorbent material in the contact portion, at the same location as the test sample or at a separate location. A third alternative involves introducing the liposome conjugate just before or directly onto the capture portion of the test device.

The migration of the test sample and liposome conjugate, if introduced outside the capture portion, is preferably assisted by introducing a wicking reagent, preferably a buffer solution, onto the strip to carry the test components along the strip. Alternatively, if the sample volume is sufficiently large, it is not necessary to employ a separate buffer solution. If the liposome conjugate is applied directly to the capture portion, the buffer solution is preferably introduced onto the strip following a period of incubation to allow reaction or hybridization of any analyte present in the test sample and the conjugate.

In constructing the test devices in accordance with the invention, it is desirable to position the capture portion relatively close to the contact portion in order to minimize the time necessary for the test mixture to reach and pass through the capture portion. However, if the test sample has not been incubated with the liposome conjugate prior to introduction onto the test device, it is important that the capture portion and the contact portion be separated sufficiently so as to provide sufficient opportunity for any analyte present in the test sample and the second binding material conjugated to the liposomes to bind to one another so that the conjugate which correlates to the amount of analyte in the test sample ultimately becomes bound in the capture portion via the analyte and the first binding material.

FIG. 1 shows a 3-pad test device in accordance with the direct measurement embodiment of the invention. It includes first, second, and third absorbent materials 104, 106, and 108, respectively, resting on support 102. Each of these absorbent materials, which are also identified functionally herein as the sample pad, reaction pad, and wicking pad, respectively, is in fluid flow contact with the adjacent absorbent pad. Sample pad 104 includes the contact portion, where the test sample and the liposome conjugate containing solution or mixture are applied. The reaction pad includes capture portion 110, to which the first binding material is non-diffusively bound.

As the test sample and conjugate mixture migrate across the device from sample pad 104 into reaction pad 106, any analyte present in the test sample binds with the second binding material conjugated to the liposomes. Because the second binding material is selected to bind with only a portion of the analyte, the analyte also remains available for binding with the first binding material, as the test components migrate into capture portion 110. In this way, a quantity of marker-loaded liposomes which is proportional to the concentration of the analyte in the test sample becomes bound in the capture portion of the test device.

Figure 3A:
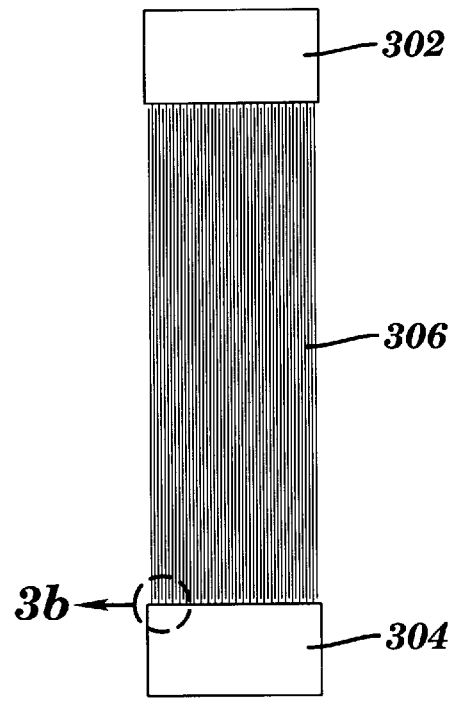
FIG. 3a is a schematic of an interdigitated electrode array employed in the test device and method of the invention.
Figure 3B:
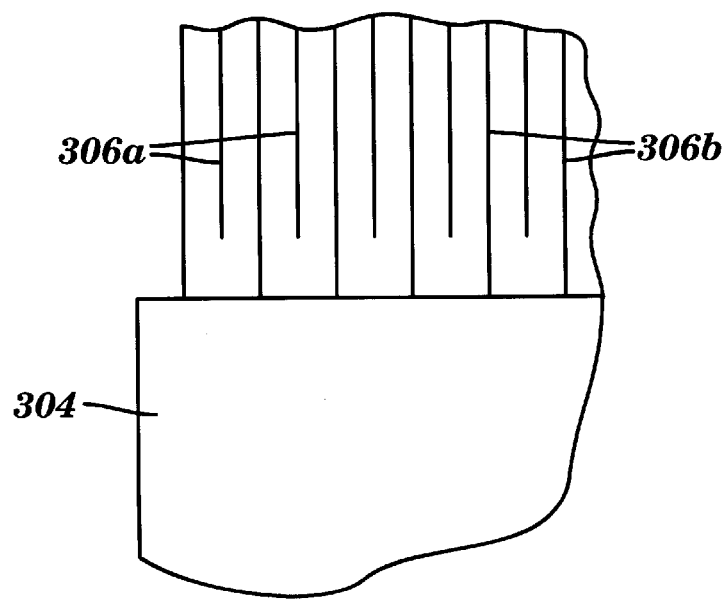

In FIG. 1, interdigitated electrode array 112, shown in greater detail in FIGS. 3a and 3b, is shown removed from its position under capture portion 110. When in place under capture portion 110, electrode array 112 is positioned to induce redox cycling of the electroactive marker released from the liposomes bound via the analyte in capture portion 110 upon lysis of the liposomes and passage of the test solution containing the released marker through absorbent material 106.

Figure 6:
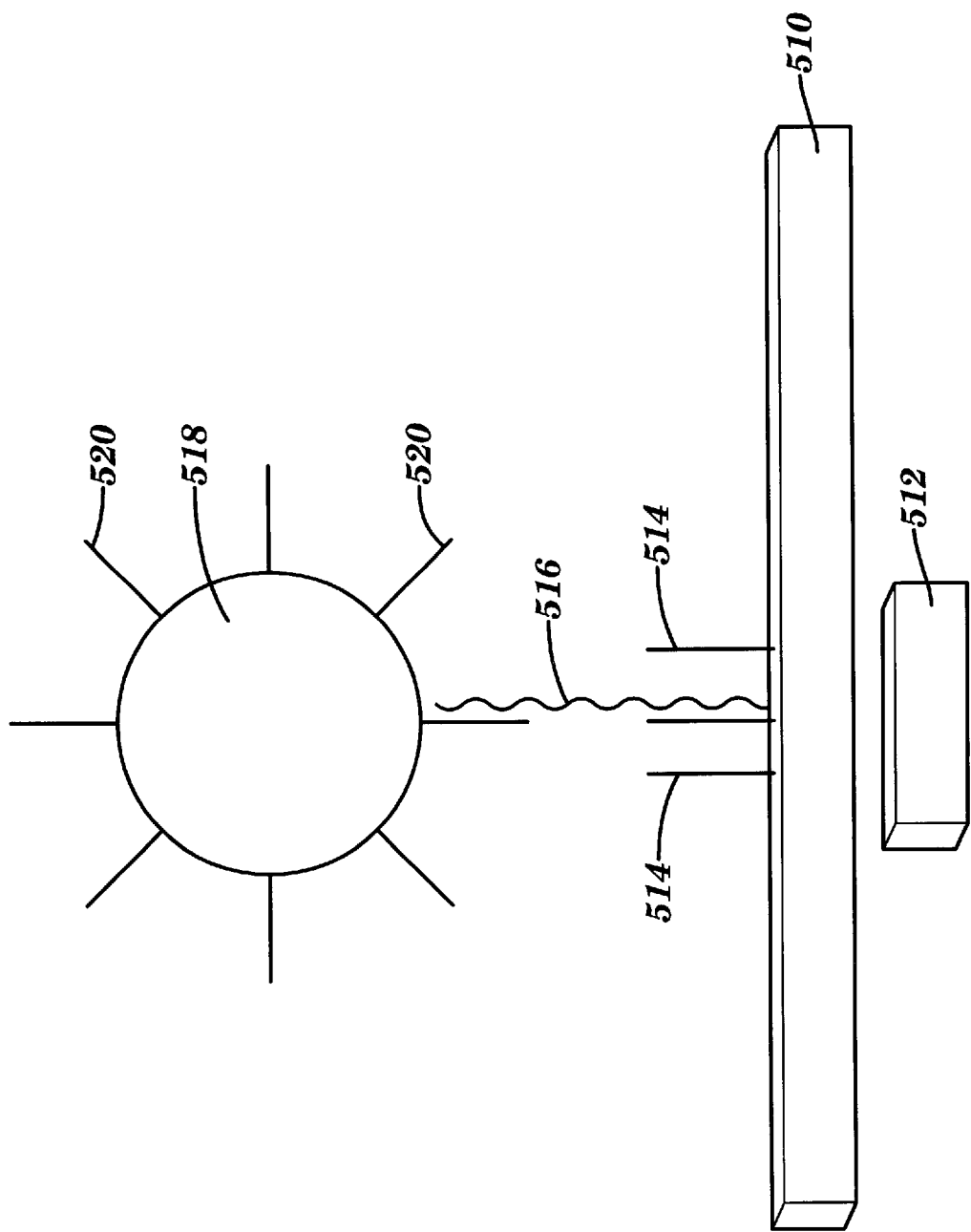
FIG. 6 is a schematic depiction of a derivatized, marker-loaded liposome captured via the target sequence and capture probe in the capture portion of the test device of the present invention.

Binding among the liposome conjugate, analyte and first binding material is depicted in FIG. 6, which is intended to depict, in particular the preferred embodiment where the analyte is a target nucleic acid sequence. In this embodiment, the first binding material is capture probe 514, which is selected to, and does, hybridize with a portion of target nucleic acid sequence 516. Capture probe 514 is immobilized in the capture portion of absorbent material 510. Second binding material 520, referred to herein as a reporter probe for the nucleic acid detection/measurement embodiment, is selected to, and does, hybridize with a portion of target nucleic acid sequence 516 other than that portion of the target with which capture probe 514 hybridizes. Second binding material 520 is conjugated to marker-encapsulating liposome 518, and binds the marker-encapsulating liposome via target nucleic acid sequence 516 and capture probe 514 to absorbent material 510 in the capture portion. Interdigitated electrode array 512 is positioned to induce redox cycling of the marker released from liposome 518 upon lysis.

A separate absorbent pad may be employed as a wicking pad, regardless of how many other absorbent pads are employed. The wicking pad serves both to pull the liquid sample and the liposome conjugate along the test strip formed by the absorbent pads, and to pull unbound conjugate out of the capture portion to enhance assay accuracy. The wicking material and pad length are preferably matched to the other components of the device and the particular test components employed in order to provide sufficient fluid flow contact along the test strip. A preferred wicking material is Whatman filter paper.

If more than one absorbent pad is employed, the pads are laid end to end, and preferably overlap slightly to ensure good fluid flow contact. The pads are preferably laminated together where they contact one another, for example, with plastic and glue. Alternatively, contact is maintained between the overlapped portions by virtue of pressure applied to the test strip by a cassette in which the test strip is held, as described herein.

Figure 5B:
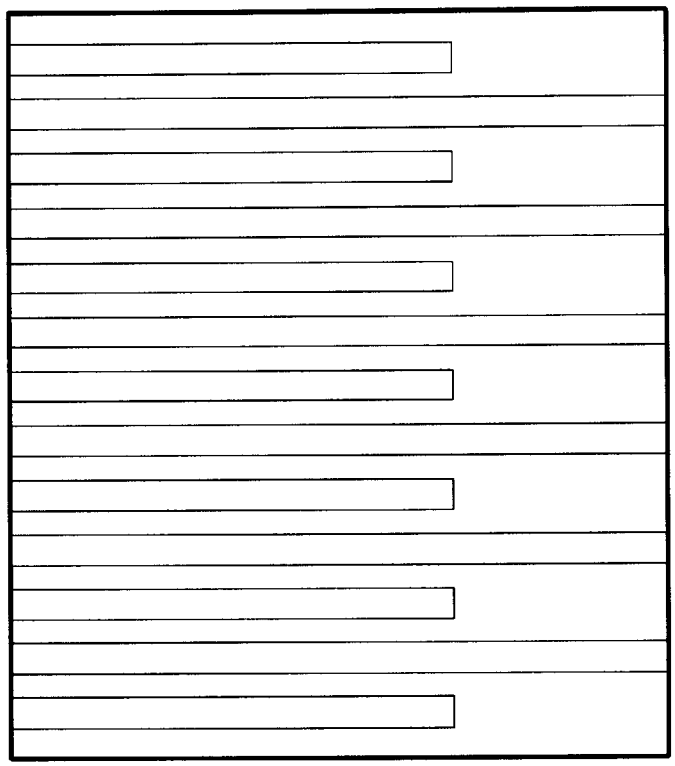
FIG. 5a and 5b are schematic depictions of interdigitated electrode arrays employed in the test device and method of the invention, at 250× and 1000× magnifications, respectively.
Figure 5A:
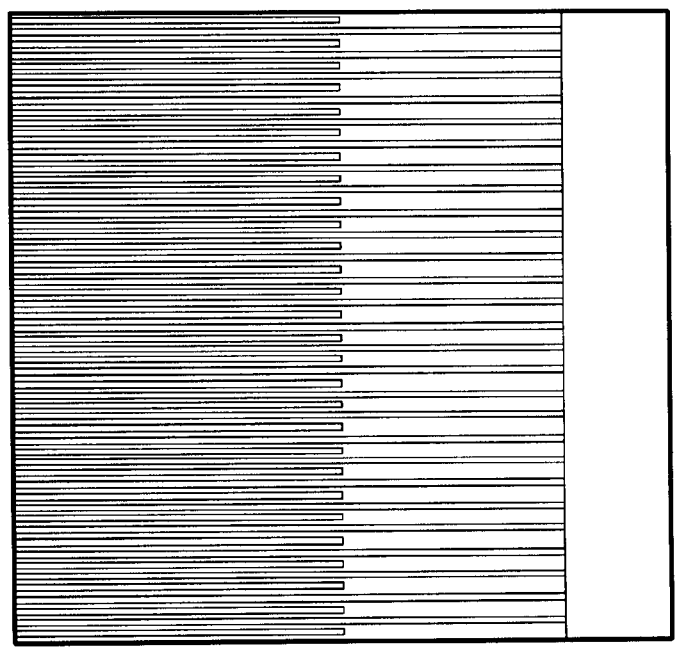

FIG. 3a shows an interdigitated electrode array employed in the test device and method of the invention. It includes anode contact pad 302 and cathode contact pad 304, and electrode fingers 306. FIG. 3b is an enlarged view of a portion of the electrode array shown in FIG. 3a. It depicts anode electrode fingers 306a interdigitated with cathode electrode fingers 306b. FIG. 5a and 5b are schematic depictions of interdigitated electrode arrays employed in the test device and method of the invention, at magnifications of 250× and 1000×, respectively.

Figure 2A:
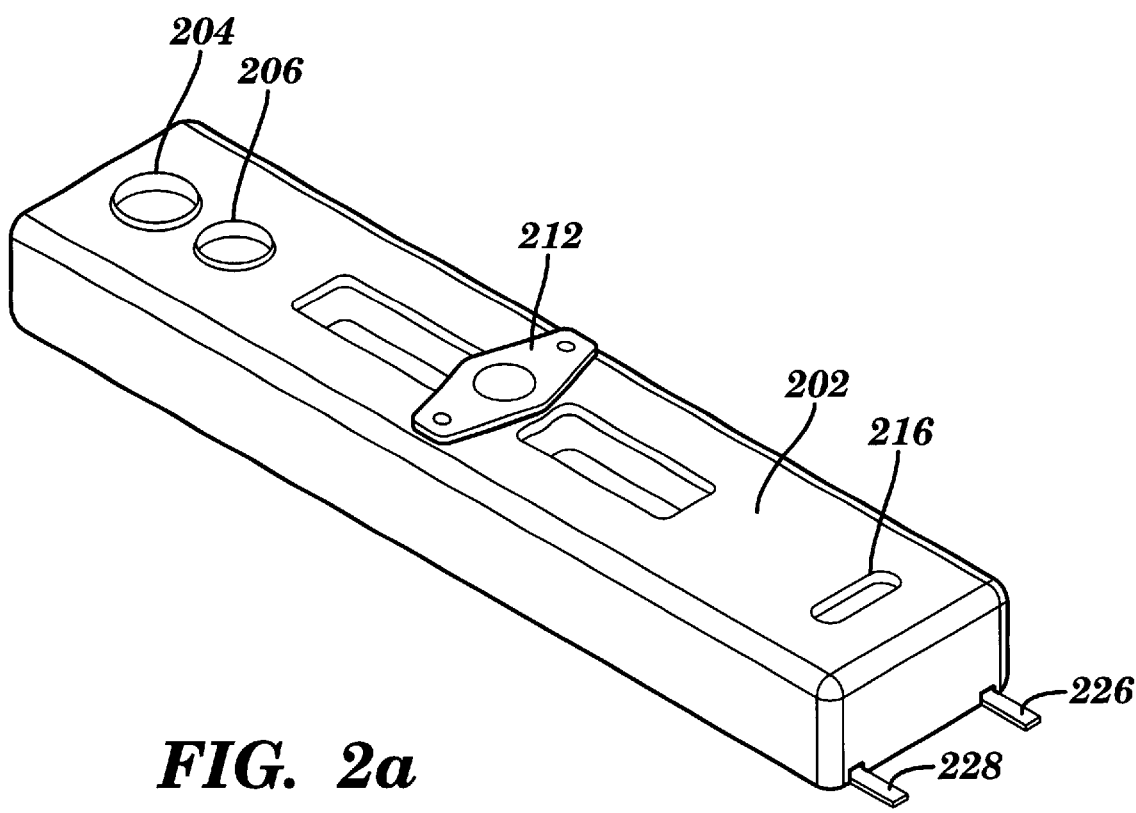
FIG. 2a is an assembled view of a cassette-enclosed test device in accordance with the invention.
Figure 2B:
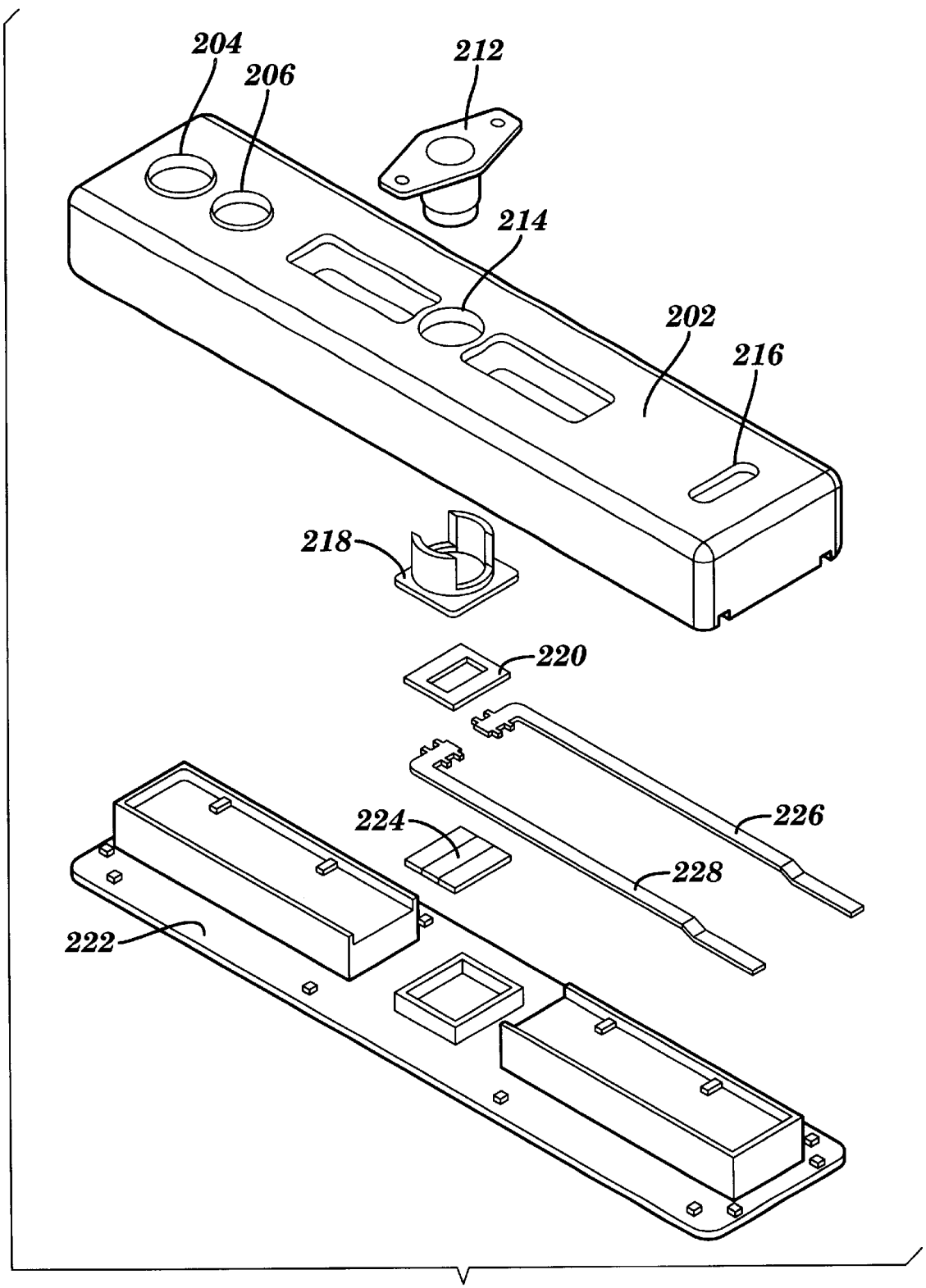

FIGS. 2a and 2b show assembled and exploded views of a cassette-enclosed test device in accordance with the invention. The cassette functions to hold the test strip in proper position and to position and support the interdigitated electrode array, as well as any protective barriers or screens protecting the electrode fingers from damage which might otherwise result from direct contact with the absorbent material of the test device. The device includes top housing 202 and bottom housing 222, which may conveniently be fabricated from plastic, for example, via injection molding techniques. Test sample and liposome conjugate may be introduced onto absorbent material 232 via buffer solution port 204 and test mixture port 206, respectively. Progress of the migration of the test components can be confirmed via opening 216.

Test accuracy can be enhanced by isolating the capture portion from the remainder of the test strip once the reaction mixture has migrated into the capture portion and the unbound conjugate has flowed past the capture portion, into a separate wicking pad, for example. For this purpose, the device shown in FIGS. 2a and 2b further includes cutting device 212 and cutting device receiver 218. Upon completion of the reaction between the analyte-liposome conjugate and the second binding material in the capture portion of the absorbent material, cutting device 212 can be used to cut through the absorbent material around the perimeter of the capture portion to physically isolate the capture portion from the adjacent portion of the absorbent material in order to ensure that only marker released from the liposomes bound via the analyte in the capture portion is measured via interdigitated electrode array 224. As cutting device 212 is pushed into cutting device receiver 218, the capture portion of the absorbent material is dropped onto gasket 220, which forms a seal preventing leakage of the liquid carried with the capture portion.

It is important to recognize that although the cutting device is shown as a circular blade in FIG. 2, the shape of the cutting device is not critical. For example, it may alternatively be a square, or comprise two parallel blades.

A voltage is applied across leads 226 and 228 to electrode array 224, which induces redox cycling of the electroactive marker released as the result of lysis of the liposomes bound to the capture portion. Liposome lysis may be achieved by introducing a liposome lysing agent through the opening in cutting device 212, preferably after the capture portion has been isolated from the adjacent absorbent material. As an alternative to application of the liposome solution or suspension at the time the assay is run, the liposome conjugate may be incorporated directly into the test strip, for example, in a dehydrated state, or dried onto the surface of the interdigitated electrode array. In these embodiments, the test mixture or test buffer provides the liquid to solubilize the lysing agent, facilitating its contact with the liposomes. The used of a liposome lysing agent in dry form avoids the addition of an additional test reagent during the assay.

Figure 4:
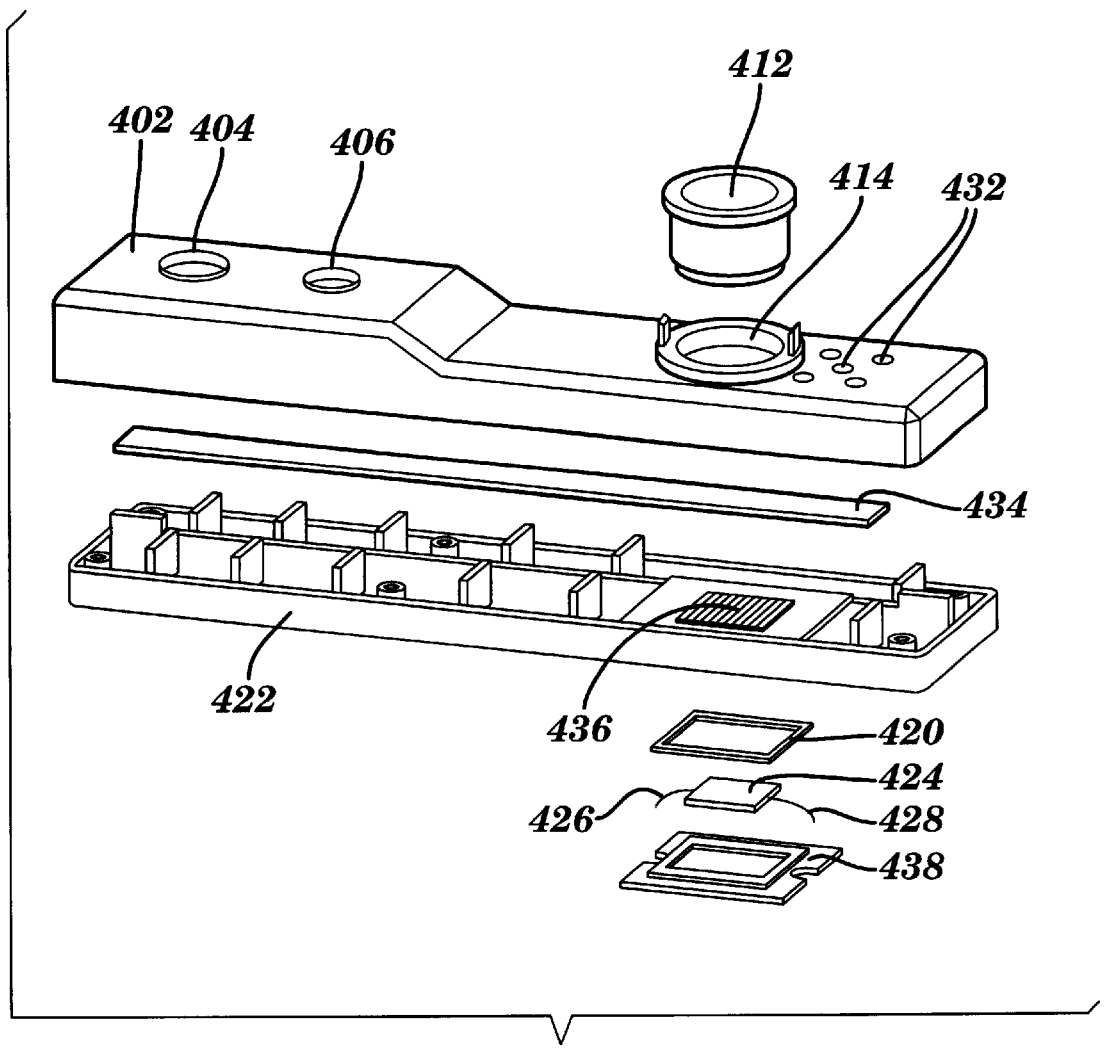
FIG. 4 is an exploded view of an alternative cassette-enclosed test device in accordance with the invention.

FIG. 4 shows an alternative cassette-enclosed test device in accordance with the invention, including buffer and test mixture openings 404 and 406, respectively, cutting device 412, cutting device receiver 414, and vent holes 432 in top housing 402. Bottom housing 422 includes optional screen 436 that physically protects interdigitated array 424 from direct contact with the capture portion of absorbent material 434 when the capture portion is cut free. Electrode array 424, connected via leads 426 and 428 to a voltage source, such as a battery and resistor, is held in position by base 438. Seal 420 prevents leakage of liquid around electrode array 424.

Although the interdigitated electrode array is shown in FIGS. 1, 2, and 4 positioned beneath the capture portion of the test device by way of example, it should be noted that all that is necessary is that the electrode array is positioned to induce redox cycling of the electroactive marker released in or flowing through the capture portion. Thus, for example, the electrode array could alternatively be laid on the upper surface of the absorbent material in the capture portion.

The test device shown in FIGS. 1, 2, and 4 can be modified to include an additional channel or channels to provide linear interpolation and verification of response. For example, a three-channel device can be constructed for the simultaneous measurement of the analyte in a test sample and high- and low-level control compositions. It should also be recognized that single channel devices are within the scope of the present invention.

Although the invention has been described as employing a two electrode array, more complicated formats can also be employed. For example, in a three electrode format, the potential of either the first or second conductor is controlled versus the reference electrode, and the potential of the other of the first or second conductors "floats" to maintain the same current through both of the electrodes. The magnitude of the current flowing between the first and second conductors is measured and correlated to the amount of the analyte, as the measured current is proportional to the marker ion concentration.

As was described above, devices in accordance with the invention can be constructed in single or multiple channel formats, depending on the desired application.

The support for the absorbent material where a support is desired or necessary will normally be hydrophobic, water insoluble, non-porous, and rigid, and usually will be of the same length and width as the absorbent strip but may be larger or smaller. A wide variety of organic and inorganic materials, both natural and synthetic, and combinations thereof, may be employed, provided only that the support does not interfere with the production of signal from the marker. Illustrative polymers include polyethylene, polypropylene, poly(4-methylbutene), polystyrene, polymethacrylate, poly(ethylene terephthalate), nylon, poly (vinyl chloride) poly(vinyl butyrate), glass, ceramics, metals, and the like.

The sizes of the pieces of absorbent material are dependent on several considerations. The following discussion is primarily focused on strips of absorbent material for purpose of illustration and not limitation. As mentioned above, other shapes such as circular, oval, trigonal, and the like, fall equally within the scope of this invention. The dimensions thereof and other parameters can be determined by those skilled in the art with reference to the disclosure herein.

When capillary flow is predominantly upward, the length and thickness of the strip control the amount of mixture that can pass through the capture portion. If the transfer of a large volume of test mixture is desired, the fluid capacity of the strip beyond the capture portion must be sufficient to accommodate the desired volume. Alternatively, an additional absorbent material, absorbing pad or sponge, referred to herein as a wicking pad, may be used to contact the end of the absorbent material beyond the capture portion. A wicking pad may be used in this manner in situations when it is desirable to pull a larger volume of the test mixture across the test device.

To permit conservation of reagents and provide for samples of limited size, the width of the strip will generally be relatively narrow, usually less than 20 mm preferably less than 10 mm. Generally, the width of the strip will not be less than about 2 mm and will usually range from about 2 mm to 10 mm, preferably from about 3 mm to 6 mm.

As is described in detail below, the test device in accordance with the invention may be modified for simultaneous multiple analyte detection or determination. The length of the strip will depend on the concentration of the analyte and practical considerations such as ease of handling and the number of measurement portions on the strip and will be about 4 cm to 20 cm, usually about 5 cm to 15 cm, preferably about 6 to 13 cm but may be of any practical length. The structure of the strip can be varied widely and includes fine, medium fine, medium, medium coarse and coarse. Selection of the porosity of the material may be based on the rate of binding of the components for a given assay.

The position of the contact and capture portions should be governed by the basic principle involved in the present invention. For example, whether the test sample and conjugate are applied to the same or separate locations in the contact portion of the test device, one desires to provide sufficient opportunity for binding to occur between the second binding material conjugated to the liposomes and any analyte present in the test sample so that the concentration of the conjugate bound in the capture portion accurately reflects the concentration of the analyte in the test sample. Generally speaking, if nitrocellulose having a pore size of 8 $\mu$m is employed for the first or first and second absorbent materials, the distance between the contact portion and the capture portion should range from about 5 mm to about 20 $\mu$m. If several capture portions are used for multi-analyte determinations, the capture portions can be grouped close together or apart but must not be so close as to compromise resolution of the signals. Consequently, such measurement portions usually should be spaced not less than 0.5 mm apart, preferably at least 1 mm apart.

The test sample may be derived from a wide variety of sources, such as physiologic fluids, illustrated by saliva, sweat, serum, plasma, urine, tear fluid, spinal fluid, etc., chemical processing streams, food, waste water, natural waters, soil extracts, etc. In carrying out the method of the invention, the sample suspected of containing the analyte may be combined with the conjugate in an electrolytic aqueous medium to form an aqueous test mixture or solution. Various addenda may be added to adjust the properties of the test mixture, or of a carrier solution used as a wicking reagent, depending upon the properties of the other components of the device, as well as on those of the liposomes or the analyte analog-liposome conjugate, or the analyte itself. Examples of solution addenda which may be incorporated into test, control, or carrier solutions or mixtures in accordance with the invention include buffers, for example, pH and ionic strength, sample or analyte solubilizing agents, such as, for example, nonpolar solvents, and high molecular weight polymers such as Ficoll®, a nonionic synthetic polymer of sucrose, available from Pharmacia, and dextran.

The contact portion of the first absorbent material is contacted with test mixture, for example, by immersing the contact portion into the test mixture. Alternatively, the test mixture may be contacted with the absorbent material by spotting the test mixture (preferably following incubation to permit reaction or hybridization) onto the absorbent material in the contact portion. Alternatively, the test sample and the conjugate, preferably in buffer solution, may be applied separately to the contact portion, either in the same location or in separate locations, as long as the two will come in contact with one another as they migrate across the absorbent material(s).

If quantitative results are desired, wetting of the first absorbent material and the second absorbent material, if present, by capillary action is allowed to continue until a sufficient volume of test mixture and/or buffer solution has passed through the capture portion to ensure that any analyte present in the test has reached the capture portion. If detection alone is desired, less care must be taken to ensure that all analyte has reached the capture portion. It is possible to "calibrate" run times and buffer volumes using pre-runs employing electrochemical detection and measurement as described herein, or colorimetric detection, as described, for example, in Rule et al. (1996) Clin. Chem. 42, 1206–1209, which is hereby incorporated by reference.

For the most part, relatively short times are involved for the test mixture to traverse the strip. Usually, traversal of the test mixture over the strip will take at least 30 seconds and not more than 45 minutes to 1 hour, more usually from about 1 minute to 10 minutes. In accordance with the method of the invention, the signal is rapidly, even immediately, detectable.

The conjugate of the second binding material and the marker-encapsulating liposomes may be prepared by procedures generally known in the art, with the particular procedure used in a given case being dependent upon the liposome components and binding material employed. Such techniques include covalent coupling, derivatization or activation, and the like. The liposomes may be produced from a component which has been derivatized with the second binding material, whereby the liposomes, when produced, are conjugated with the second binding material. In another procedure, the liposomes, including the marker, may be initially formed, followed by conjugating the liposomes with the second binding material by procedures known in the art.

Liposomes can be prepared from a wide variety of lipids, including phospholipids, glycolipids, steroids, relatively long chain alkyl esters; e.g., alkyl phosphates, fatty acid esters; e.g. lecithin, fatty amines, and the like. A mixture of fatty materials may be employed, such as a combination of neutral steroid, a charge amphiphile and a phospholipid. Illustrative examples of phospholipids include lecithin, sphingomyelin, and dipalmitoylphosphatidylcholine, etc. Representative steroids include cholesterol, chlorestanol, lanosterol, and the like. Representative charge amphiphilic compounds generally contain from 12 to 30 carbon atoms. Mono- or dialkyl phosphate esters, or alkylamines; e.g. dicetyl phosphate, stearyl amine, hexadecyl amine, dilaurylphosphate, and the like are representative.

The liposome sacs are prepared in aqueous solution containing the marker whereby the sacs will include the electroactive marker in their interiors. The liposome sacs may be prepared by vigorous agitation in the solution, followed by removal of the unencapsulated marker. Further details with respect to the preparation of liposomes are set forth in U.S. Pat. No. 4,342,826 and PCT International Publication No. WO 80/01515, both of which are incorporated by reference.

As hereinabove indicated, the signal producing system includes an electroactive marker included in the interior of the conjugated liposomes. Suitable markers are those which are electrochemically active but will not degrade the liposomes or otherwise leach out of the liposomes. They include metal ions, organic compounds such as quinones, phenols, and NADH, and organometallic compounds such as derivatized ferrocenes. A reversible ferrocyanide-ferricyanide couple is the most preferred electroactive marker in accordance with the invention. An equal mixture of ferrocyanide and ferricyanide is particularly preferred.

The use of liposomes as described in the present application provides several advantages over traditional signal production systems employing, for example, enzymes. These advantages include increased signal intensity, shelf stability, and instantaneous release of signal-producing markers, as described in T. A. Siebert, S. G. Reeves, R. A. Durst, *Analytica Chimica Acta* 282, 297–305 (1993); W. T. Yap, L. Locascio-Brown, A. L. Plant, S. J. Choquette, *Analytical Chemistry* 63, 2007 (1991); A. L. Plant, M. V. Brizgys, L. Locasio-Brown, R. A. Durst, *Analytical Biochemistry* 176, 420–426 (1989); L. Locascio-Brown, A. L. Plant, V. Horvath, R. A. Durst, *Analytical Chemistry* 62, 2587–2593 (1990); and R. A. Durst, L. Locascio-Brown, A.

L. Plant, R. D. Schmid, Eds., *Flow Injection Analysis based on enzymes or antibodies*, vol. 14 (VCH, Weinheim, 1990), each of which is hereby incorporated by reference. For example, initial calculations indicate that the rupture of a single liposome in a typical capillary electrophoresis sample volume would lead to a concentration of 5 $\mu$M $K_4Fe(CN)_6$ at the interdigitated electrode array detector. Therefore, due to the great sensitivity of the interdigitated electrode arrays, the detection of single liposome events should be theoretically possible with the present system.

As described above, lysis of the liposomes in the capture portion may be accomplished by applying a liposome lysing agent to the capture portion of the absorbent material after the conjugate becomes bound therein. Suitable liposome lysing materials include surfactants such as octylglucopyranoside, sodium dioxycholate, sodium dodecylsulfate, polyoxyethylenesorbitan monolaurate sold by Sigma under the trademark Tween-20, and a non-ionic surfactant sold by Sigma under the trademark Triton X-100, which is t-octylphenoxypolyethoxyethanol. Octylglucopyranoside is a preferred lysing agent for many assays, because it lyses liposomes rapidly and does not appear to interfere with signal measurement. Alternatively, complement lysis of liposomes may be employed, or the liposomes can be ruptured with electrical, optical, thermal, or other physical means.

The movement of the test components along the absorbent material(s) is due to capillary action. This capillary movement along the absorbent material causes the test mixture to be carried to and through the capture portion, where measurement of the marker released from the liposomes takes place.

An electroactive species, such as ferrocyanide, is encapsulated in the liposomes. The interdigitated electrode array is positioned to induce redox cycling of an electroactive marker released in the capture portion.

The reference electrode, if employed, will usually be a silver electrode, although lead may alternatively be used for the reference electrode. The electrodes forming the interdigitated array may be prepared from any suitable materials such as the noble metals, other metals such copper and zinc, or carbon electrode materials in various forms, including graphitic, glassy and reticulated carbon materials, or suitable mixtures of these materials. The first conductor may be composed of the same or a different material from the second conductor.

The electrochemical detection system of the present invention comprises an interdigitated set of microelectrodes, and, optionally, a reference electrode. In another optional embodiment, a "four-electrode" system comprising the interdigitated array, a reference electrode, and an auxiliary electrode can be employed. A four-electrode system is described in O. Niwa, M. Morita, H. Tabei, Anal. Chem. 62, 447–452 (1990). Platinum is a suitable material for the auxiliary electrode.

The interdigitated electrode set can be fabricated on a support, such as a thermally oxidized silicon wafer by photolithography and the lift off technique described in Aoki, A; Matsue, T.; Uchida, I. Analytical Chemistry 1990, 62, 2206–10, which is hereby incorporated by reference. We have found that better results can be obtained by incorporating silicon nitride ($Si_3N_4$) on top of the oxidized silicon support. Specifically, the silicon nitride appears to provide better insulation, which is important because of the ion solution environment employed in the present method and device. See also K. Aoki, M. Morita, O. Niwa, H. Tabei, Journal of Electroanalytical Chemistry 256, 259 (1988) and Aoki, A. M., Tomokazu; Uchida, Isamu, Analytical Chemistry 1990, 62, 2206–10, which are also hereby incorporated by reference. Platinum interdigitated electrodes are preferably formed by evaporation and the lift-off technique described by Aoki. Silver lead patterns, and a platinum electrode and silver reference electrode, if used, are preferably formed by photolithography and the lift-off technique. If possible, all lead wires, preferably composed of silver, should be located distal to the surface of the interdigitated array.

Electrodes as described herein have been fabricated at the Cornell Nanofabrication Facility (Ithaca, N.Y.). Separate photomasks are drawn for silver and platinum materials. However, only a single mask is required for the fabrication of a two electrode array.

The electrode set formed on the silicon wafer can then be applied directly to the surface of the absorbent material. Borosilicate glass and quartz substrates may alternatively be employed. Such substrate-backed electrodes can be removed from the strip after the assay is complete and prepared for re-use if desired. If electrodes are to be re-used, it is often preferable to coat them with a protective polymer layer. Agarose, for example, can be used to prevent passivation of electrodes.

In a preferred embodiment, each electrode set has an overall size of 9×4 mm and is approximately 350 $\mu$m thick. The actual area of interdigitation is 6 mm×2 mm and is designed to fit conveniently across 5 mm wide immunomigration strips. This arrangement allows for the array to completely straddle the absorbent material, maximizing the interaction of electroactive marker with the electrodes, and, therefore, assay sensitivity. A preferred interdigitated array consists of 200 pair of 3 $\mu$m wide microelectrode fingers separated by a 1–5 $\mu$m gap. Preferred reference and auxiliary electrodes are 7×1 mm.

Although the preferred configuration is described above, the first conductor and said second conductor may comprise from 2 to 1000 fingers, and the fingers of said first and second conductors can range in size from about 1 $\mu$m to about 20 $\mu$m wide. The electrode fingers can be spaced from about 0.5 $\mu$m to about 10 $\mu$m apart.

Each of the electrodes may alternatively be prepared by screen printing of the electrode materials onto the absorbent material, although with screen printing, the interelectrode distance may be on the order of 50 $\mu$m to 0.1 mm. As is well known, screen printing involves preparation of an organic or aqueous slurry of the electrode material, typically, a fine powder of carbon, gold, etc., followed by application of the slurry across and through a silk screen onto the absorbent material of the test device. This slurry may optionally include a polymeric binder which aids in aggregating the fine metallic particles together on the surface of the absorbent material. The electrode material slurry may be fixed on the surface of the absorbent material by heating, however, the printed electrode portions are preferably allowed to air dry on the surface of the absorbent material.

The test components and any control mixtures are electrolyte solutions such as saline solutions of the analyte and conjugate.

In the method of the invention, a fixed voltage is applied across the conductors to induce redox cycling of the electroactive marker released from the liposomes captured in the capture portion. A simple battery can be used to apply the voltage. Other devices which may be used as potentiostats in accordance with the invention include the Cypress (Lawrence, Kans.) System Electrochemical Analyzer (CS-1090) and the BAS (West Lafayette, Ind.) Amperometric Detector (LC-4C, LC-3C, LC-3D).

The solvent for the test sample will normally be an aqueous medium, which may be up to about 40 weight percent of other polar solvents, particularly solvents having from 1 to 6, more usually of from 1 to 4, carbon atoms, including alcohols, formamide, dimethylformamide and dimethylsulfoxide, dioxane and the like. Usually, the cosolvents will be present in less than about 30–40 weight percent. Under some circumstances, depending on the nature of the sample, some or all of the aqueous medium could be provided by the sample itself.

The pH for the medium will usually be in the range of 4–10, usually 5–9, and preferably in the range of about 6–8. The pH is chosen to maintain a significant level of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is usually not critical when the analyte is other than a nucleic acid, but in individual assays, one buffer may be preferred over another. For nucleic acid analytes, it is necessary to choose suitable buffers. Such buffers include SSC, a sodium chloride, sodium citrate buffer, and SSPE (sodium chloride, sodium phosphate, EDTA).

The concentration of electrolytes in the medium will usually be adjusted to achieve isotonicity or equi-osmolality with the solution in the interior of the liposomes to prevent their crenation or swelling.

With some increased complexity of the excitation waveform applied by the electroanalyzer, electrochemical measurement in accordance with the invention may also be carried out using stripping voltammetry, employing, for example, liposome encapsulated metal ions for detection and measurement.

Moderate, and desirably substantially constant, temperatures are normally employed for carrying out the assay. The temperatures for the assay and production of a detectable signal will generally be in the range of about 4–65° C., more usually in the range of about 20–38° C., and frequently, will be about 15–45° C.

The concentration, in the liquid sample, of analyte which may be assayed will generally vary about $10^{-3}$ to about $10^{-20}$M, more usually from about $10^{-5}$ to about $10^{-15}$M. Considerations such as the concentration of the analyte of interest and the protocol will normally determine the concentration of the other reagents.

With the test device and method of the invention, one may also assay a test sample for a plurality of analytes such as toxic chemicals or pathogens, or screen for one or more of a plurality of analytes. In one embodiment, the test device includes multiple capture portions and corresponding sets of interdigitated electrode arrays. By appropriately controlling the potentials at the electrodes, different marker ions can be measured and referred back to separate analyte concentrations. In another embodiment, a single set of electrodes, preferably in a three-electrode configuration as described above. The potential is varied, for example, by scanning linearly with time, to produce currents proportional to the different ion concentrations at unique potentials (times).

As a matter of convenience, the present device can be provided in a kit in packaged combination with predetermined amounts of reagents for use in assaying for an analyte or a plurality of analytes. Aside from the absorbent test device and the liposome conjugate, other additives such as ancillary reagents may be included, for example, stabilizers, buffers, and the like. The relative amounts of the various reagents may be varied widely, to provide for concentration in solution of the reagents which substantially optimize the sensitivity of the assay. The reagents can be provided as dry powders, usually lyophilized, including excipients, which on dissolution will provide for a reagent solution having the appropriate concentrations for performing the assay. The kit or package may include other components such as standards of the analyte or analytes (analyte samples having known concentrations of the analyte).

The present invention is applicable to procedures and products for determining a wide variety of analytes. As representative examples of types of analytes, there may be mentioned: environmental and food contaminants, including pesticides and toxic industrial chemicals; drugs, including therapeutic drugs and drugs of abuse; hormones, vitamins, proteins, including antibodies of all classes; prions; peptides; steroids; bacteria; fungi; viruses; parasites; components or products of bacteria, fungi, viruses, or parasites; aptamers; allergens of all types; products or components of normal or malignant cells; etc. As particular examples, there may be mentioned $T_4$; $T_3$; digoxin; hCG; insulin; theophylline; leutinizing hormones and organisms causing or associated with various disease states, such as streptococcus pyrogenes (group A), Herpes Simplex I and II, cytomegalovirus, chlamydiae, etc. The invention may also be used to determine relative antibody affinities, and for relative nucleic acid hybridization experiments, restriction enzyme assay with nucleic acids, and binding of proteins or other material to nucleic acids.

As hereinabove indicated, the assay may be qualitative (presence or absence of certain level of analyte) or quantitative or semi-quantitative. The preparation of suitable standards and/or standard curves is deemed to be within the scope of those skilled in the art from the teachings herein.

The method of the invention, and preparation and use of the test device in accordance with the invention, are illustrated by the following Examples.

EXAMPLES

Materials for Example 1

Materials used:
  Qiagen RNeasy Kit for RNA purification (Qiagen Company, Germany)
  Boom technology (Organon Teknika, Netherlands)

Example 1

Nucleic Acid Extraction a. Heat Shock Optimization
  Oocysts were subjected to 41° C.–47° C. in a water bath or heating block for up to 20 min.
b. Oocyst Disruption to Form Oocyst Lysates
  The following disruption methods were studied: freeze/thaw cycling (liquid $N_2$/65° C.), bead beating with subsequent freeze/thaw cycling, incubation at 95° C., incubation at 55° C., and incubation at 60° C. The following experimental work was carried out using samples prepared via the freeze/thaw cycling.
c. Nucleic Acid Purification
  For the nucleic acid extraction from the oocyst lysates two commercially available methods were used. The Qiagen procedure, described in the RN-easy Mini Handbook, March 1997 (Qiagen Inc., 28159 Avenue Stanford, Valencia, Calif. 91355), which is hereby incorporated by reference, was varied in order to find optimal conditions. Specifically, an additional ethanol washing step and longer drying time were employed. The Boom technique, described in R. Boom et al, "Rapid and Simple Method for Purification of Nucleic Acids" J. Clin. Microbiol., March 1990, 495–503, which is hereby incorporated by reference, was used following the protocol.

Example 2

NASBA Amplification

The *C. parvum* sequence is disclosed in N. V. Khramtsov et al., "Cloning and analysis of a *Cryptosporidium parvum* Gene Encoding a Protein with Homology to Cytoplasmic Form Hsp70" J. Euk. Microbiol., 42(4), 1995, 416–422, which is hereby incorporated by reference. The nucleic acid was amplified using OT NASBA amplification kits. *C. parvum* specific primer was designed and utilized in the amplification kit. The standard conditions were varied in respect of the KCl concentration and the incubation time to find optimal conditions. Amplifications were carried out for 60–90 min.

Example 3

Interdigitated Ultramicroelectrode Array (IDUA or IDA) Preparation a. IDUA Preparation IDUAs were prepared using the following techniques: photolithography and lift-off. IDUAs were made on 3' silicon wafers. Preparation was as described in copending U.S. patent application Ser. No. 08/722,901, except that the silicon wafers were not only coated with a silicon oxide layer, but additionally with a silicon nitride layer in order to improve the insulation of the silicon.

On top of this silicon nitride layer, the IDUA structure was built. The IDUAs were made of gold or platinum (including a first layer of 5 nm titanium layer, which ensures a good contact of the metals to the silicon nitride). IDUAs were treated with an oxygen plasma after the lift-off technique. This plasma is used to clean the metal surfaces from left over photo resists. However, it had a negative effect on the platinum surface, since it became oxidized and less active for electrochemical experiments. Non plasma treated platinum electrodes were electrochemically the best and were used for most of the experiments.

Designs were prepared with and without additional electrodes for use as reference and auxiliary electrodes in electrochemical experiments. It was found that the additional electrodes were not required and the last IDUA iterations were made with the IDUA only.

b. Electrochemical Characterization of the IDUAs

The IDUAs were electrochemically characterized using amperometry and cyclic voltammetry analyzing the reversibly oxidizable Redox couple ferrohexacyanide/ferrihexacyanide. The applied potential was varied.

Figure 13:
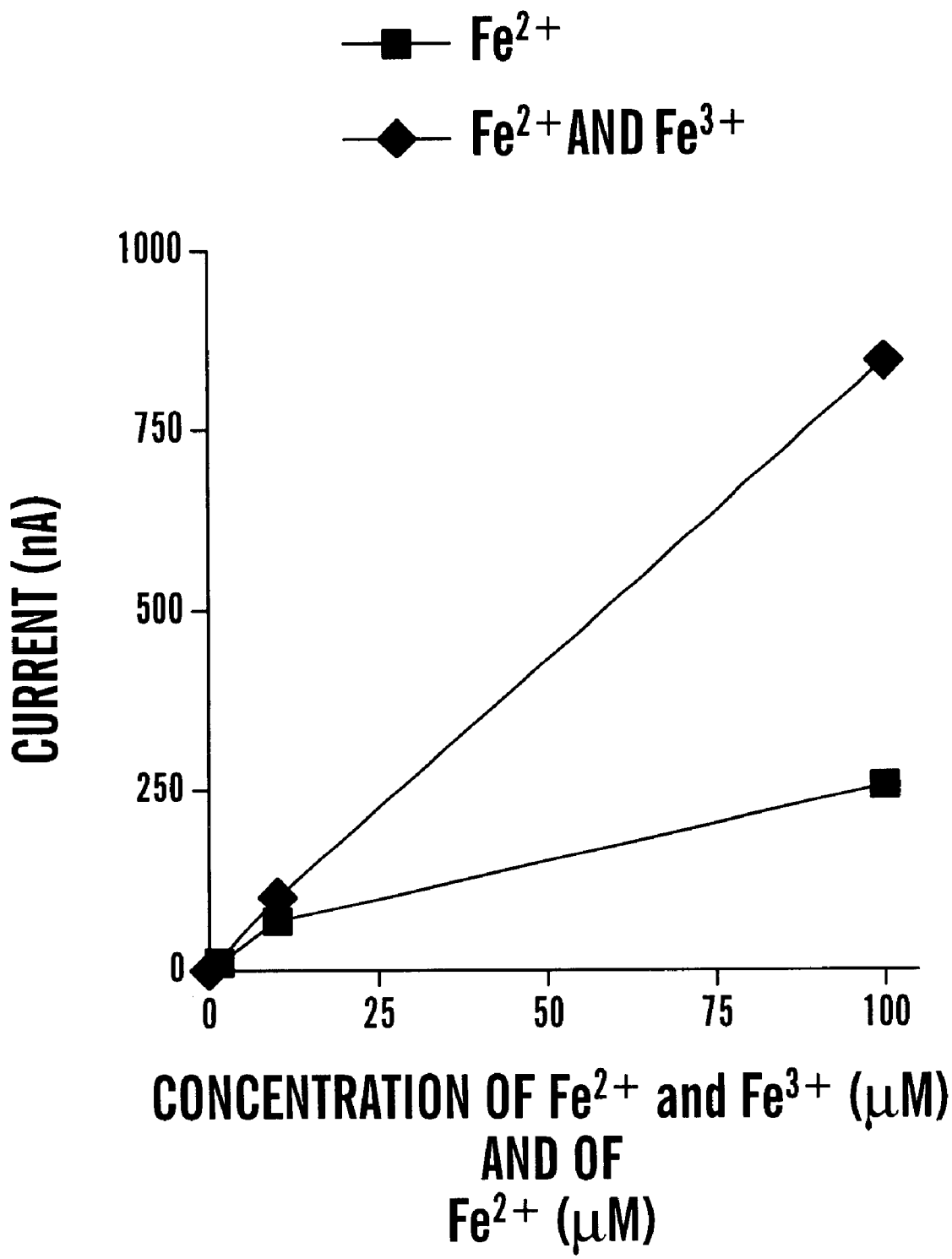
FIG. 13 is a graph of current generated versus electroactive marker concentration for ferrocyanide versus a mixture of ferrocyanide and ferricyanide.

Standard curves of ferrohexacyanide versus the same volume of a 1:1 mixture of ferrohexacyanide and ferrihexacyanide were compared. It was found that the mixture gave significantly higher currents at the same concentrations due to an increased cycling of the analytes at the IDUA surface, as shown in FIG. 13. In later experiments, and equal mixture of ferrihexacyanide and ferrohexacyanide was used.

The different IDUA iterations shown in Table 2 were compared by detecting different concentrations of a mixture of ferrohexacyanide/ferrihexacyanide at a potential of 400 mV.

TABLE 2

|  | IDUA 1 | IDUA 2 | IDUA 3 | IDUA 4 |
| --- | --- | --- | --- | --- |
| Fingers per set | 100 | 200 | 200 | 200 |
| Width of finger | 3 µm | 2 µm | 3 µm | 3 µm |
| Width of gap | 2 µm | 1 µm | 2 µm | 2 µm |
| Array area | 3.0 mm$^2$ | 4.0 mm$^2$ | 6.6 mm$^2$ | 6.6 mm$^2$ |
| Layer height | 300 nm | 300 nm 150 nm | 150 nm | 150 nm |
| Metal | gold | gold | gold platinum | gold platinum |

Figure 7:
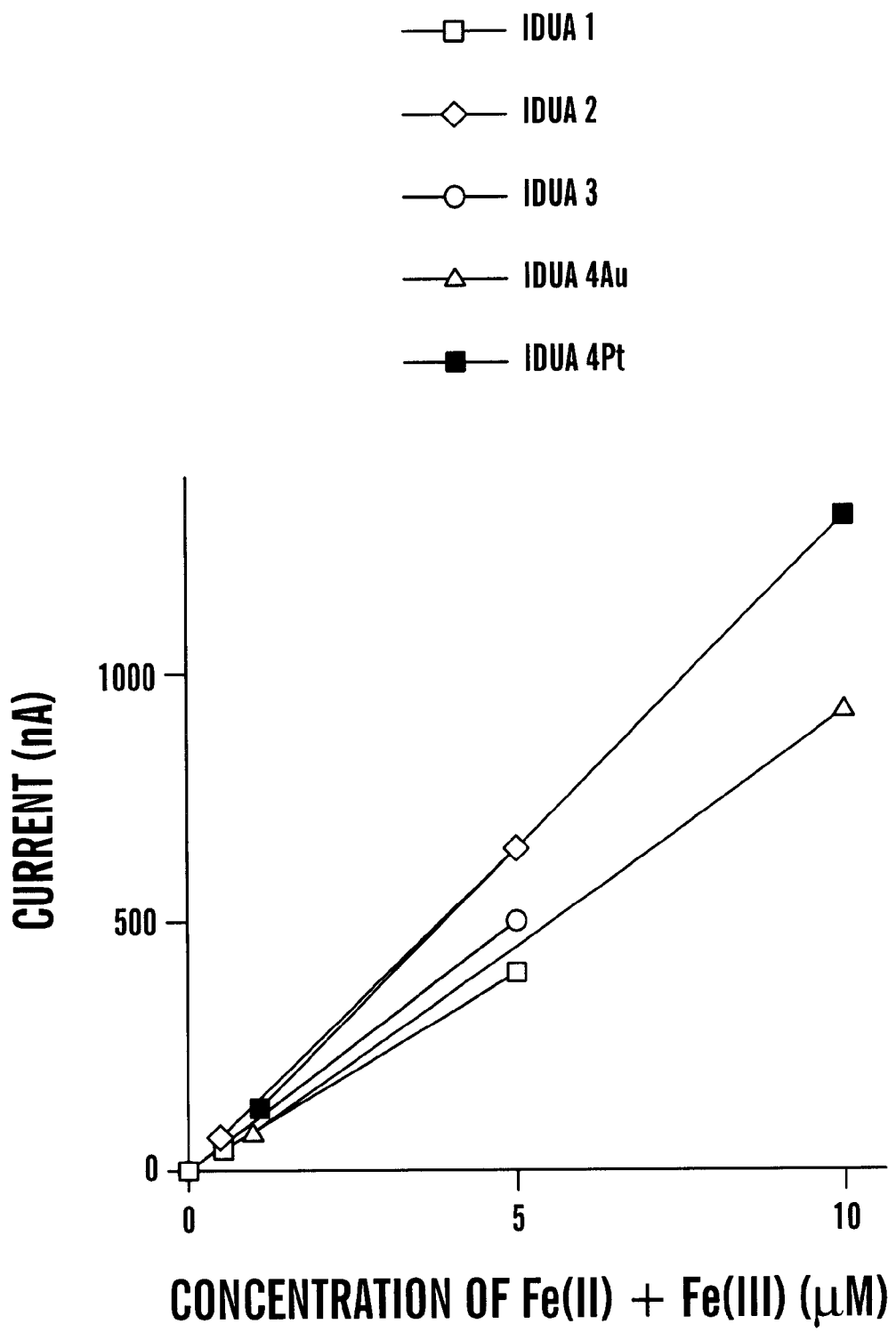
FIG. 7 is a graph of current generated versus marker concentration for 5 different interdigitated electrode array configurations.

The results of these experiments are shown in FIG. 7 (the data shown in FIG. 7 were prepared using a 150 nm gold layer in Iteration 2). IDUAs of iteration 4 made of platinum were chosen for the use as the transducer in the biosensor.

Figure 8:
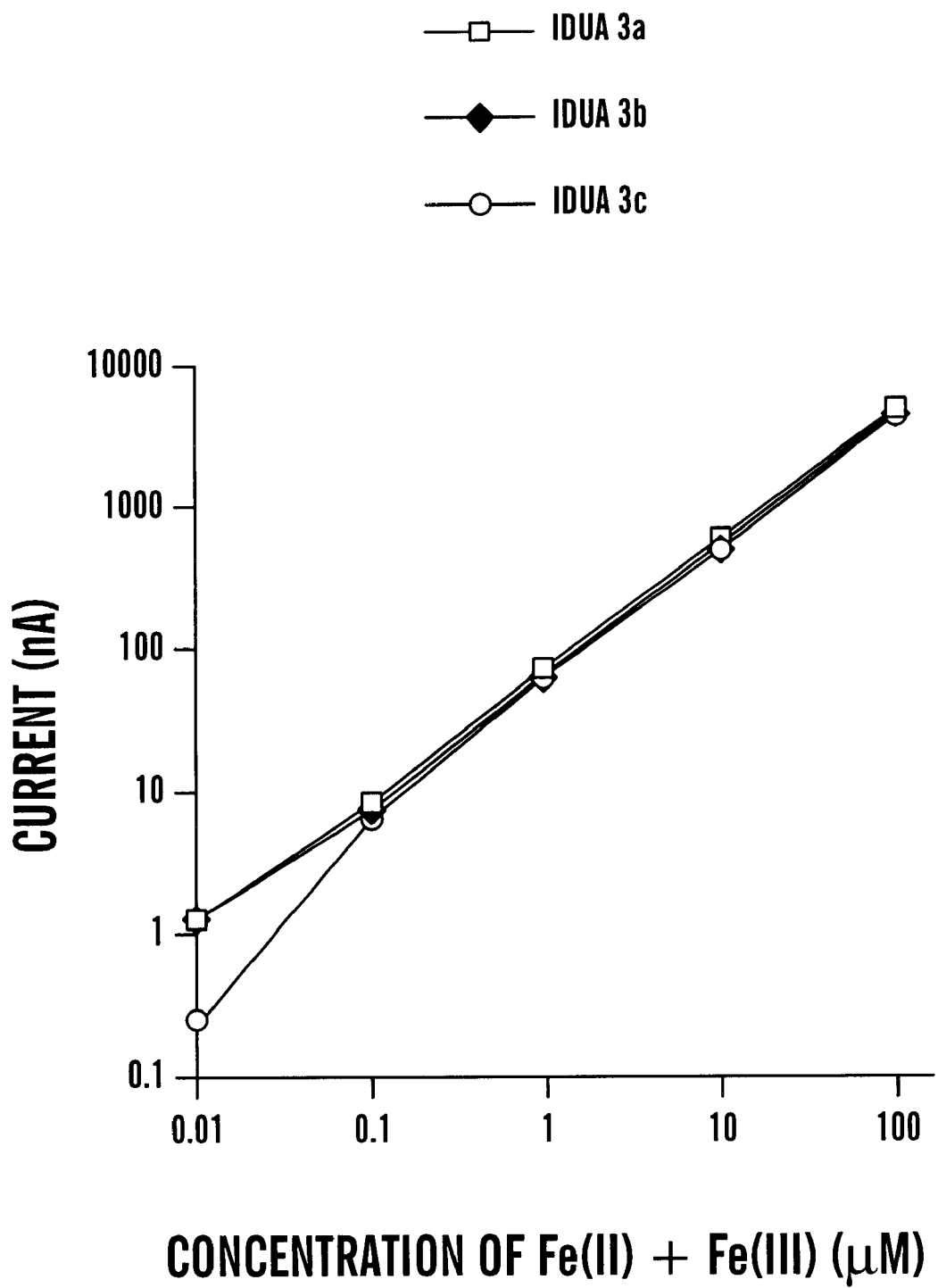
FIG. 8 is a graph of current generated versus marker concentration for 3 separate interdigitated electrode arrays of the same size and composition.

The reproducibility of the IDUAs was tested detecting different concentrations of a mixture of ferrohexacyanide/ferrihexacyanide at a potential of 400 mV, as shown in FIG. 8. Three IDUAs of the 3$^{rd}$ iteration shown in Table 2 made of gold were used for this experiment.

As shown in Table 3, it was found that the IDUAs are at least 20 times more sensitive than conventional (non-interdigitated) microelectrodes with the same surface area and give an at least 8 times higher signal for the same concentration measured.

TABLE 3

|  | Interdigitated Electrode Array | Conventional Microelectrode |
| --- | --- | --- |
| Detection Limit | 0.01 µM | 0.2 µM |
| Signal Intensity at 10 µm | 150 nA | 19 nA |

The effect of different detergents and buffer concentrations were investigated with the IDUAs. It was found that the detection of ferrohexacyanide/ ferrihexacyanide was influenced by the ionic strength of the buffer. A 0.25 M phosphate buffer was chosen to be optimal. Different detergents that were investigated gave a high background signal at 400 mV. Finally, a pure b-octyl glucopyranosid (OG) was chosen as the optimal detergent, since the background signal was minimal, similar to pure buffer solution.

Example 3

Liposome Preparation

Liposomes were prepared following the procedures described in U.S. Pat. Nos. 5,789,154; 5,756,362; and 5,753,519; and U.S. patent application Ser. No. 08/722,901, the disclosures of which are hereby incorporated by reference. Oligonucleotides, specific for the target sequence, were covalently coupled to the outside of the liposome membrane.

Example 4

Membrane Strip Preparation, Assay Run, Detection

The membrane strips were prepared as described in U.S. Pat. Nos. 5,789,154; 5,756,362; 5,753,519; and copending U.S. patent application Ser. No. 08/722,901, except that a 2 piece-assembly (nitrocellulose and Whatmann filter paper) and a 3-piece assembly (DuPont Sontara™, nitrocellulose, and Whatmann filter paper) were utilized as well as a 1-piece assembly (nitrocellulose).

Thus, the absorbent material of the 1-piece assembly was the same as the $1^{st}$ material used for the 2-piece assembly and the middle piece of the 3-piece assembly. The wicking material used as the second material in the 2-piece assembly was the same used as the third material in the 3-piece assembly. Dimensions of the various pieces varied.

The absorbent material was used for the immobilization of the oligonucleotides. It was coated with a blocking solution subsequent to the immobilization procedure. The material of the 3-piece assembly used as first piece was coated with a blocking solution as well. The wicking material was used untreated.

The oligonucleotides were immobilized directly onto the absorbent material or as biotinylated oligonucleotides via streptavidin binding in the capture portion.

The strips were used in a vertical or horizontal way for the experiments. They were dipped into the sample solution or sample solution was applied to the first piece of the assemblies—before the capture portion or directly onto it. A sample buffer was applied subsequently onto the beginning of the $1^{st}$ piece of the strips (directly or after several minutes incubation time) to allow migration on the strip to occur and the sample to pass the capture portion.

Subsequently, as soon as all sample buffer migrated along the strip, the capture portions was used for detection. In one trial, the capture portion was cut out and laid on top of an IDUA, a detergent was added and the signal detected after a few minutes. In an alternative trial, the capture portion was cut out and laid on top of an IDUA which had dried detergent on its surface, and the signal was detected after a few minutes. When sulforhodamine B (SRB) encapsulating liposomes were used, the signal was detected using a scanner.

Figure 11:
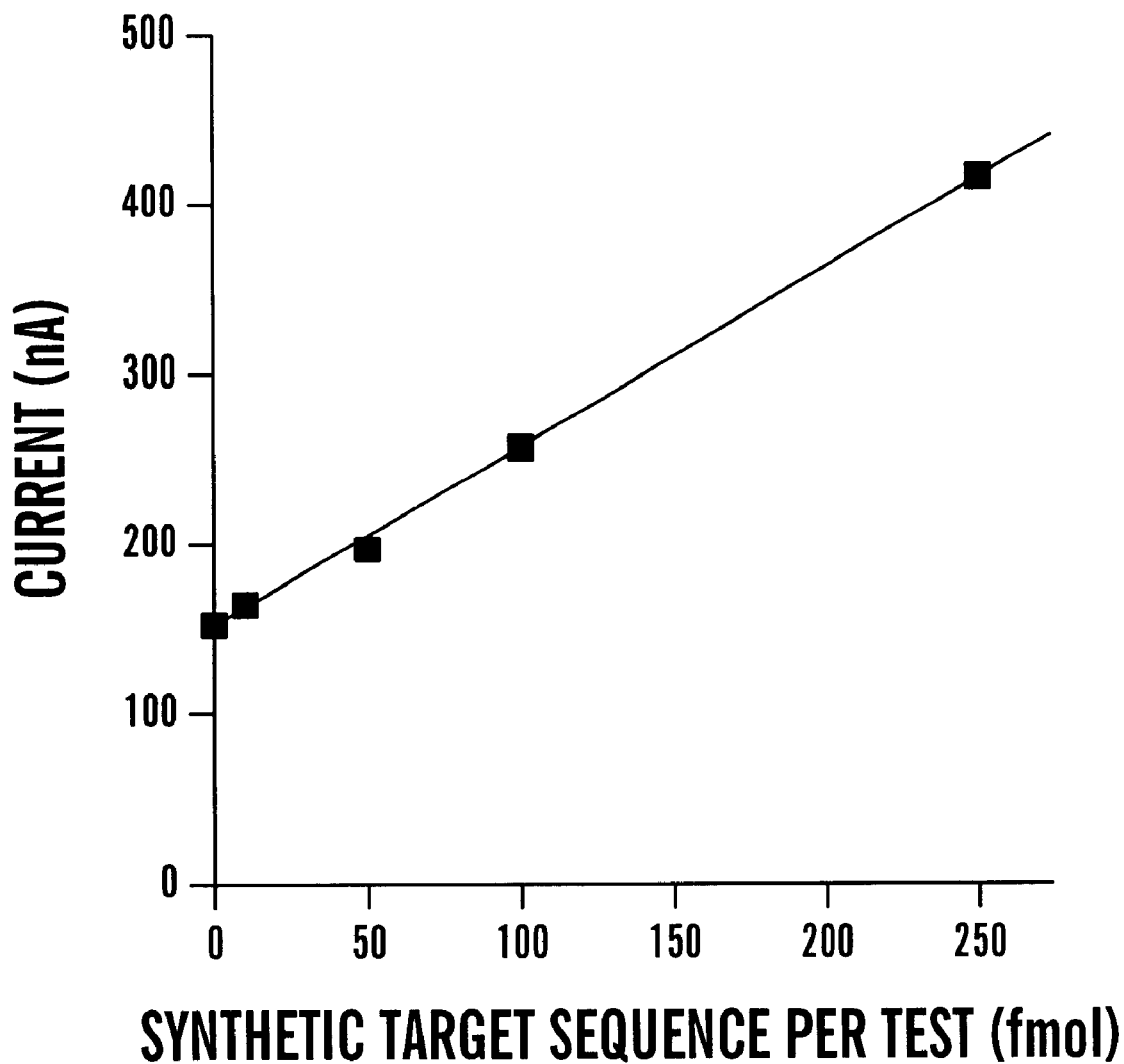
FIG. 11 is a graph of current generated versus synthetic target sequence concentration using two-pad test strip.

Different concentrations of a synthetic target sequence were detected using a 2-pad assembly, with introduction of liposomes directly onto the capture portion. The results are shown in FIG. 11.

Figure 12:
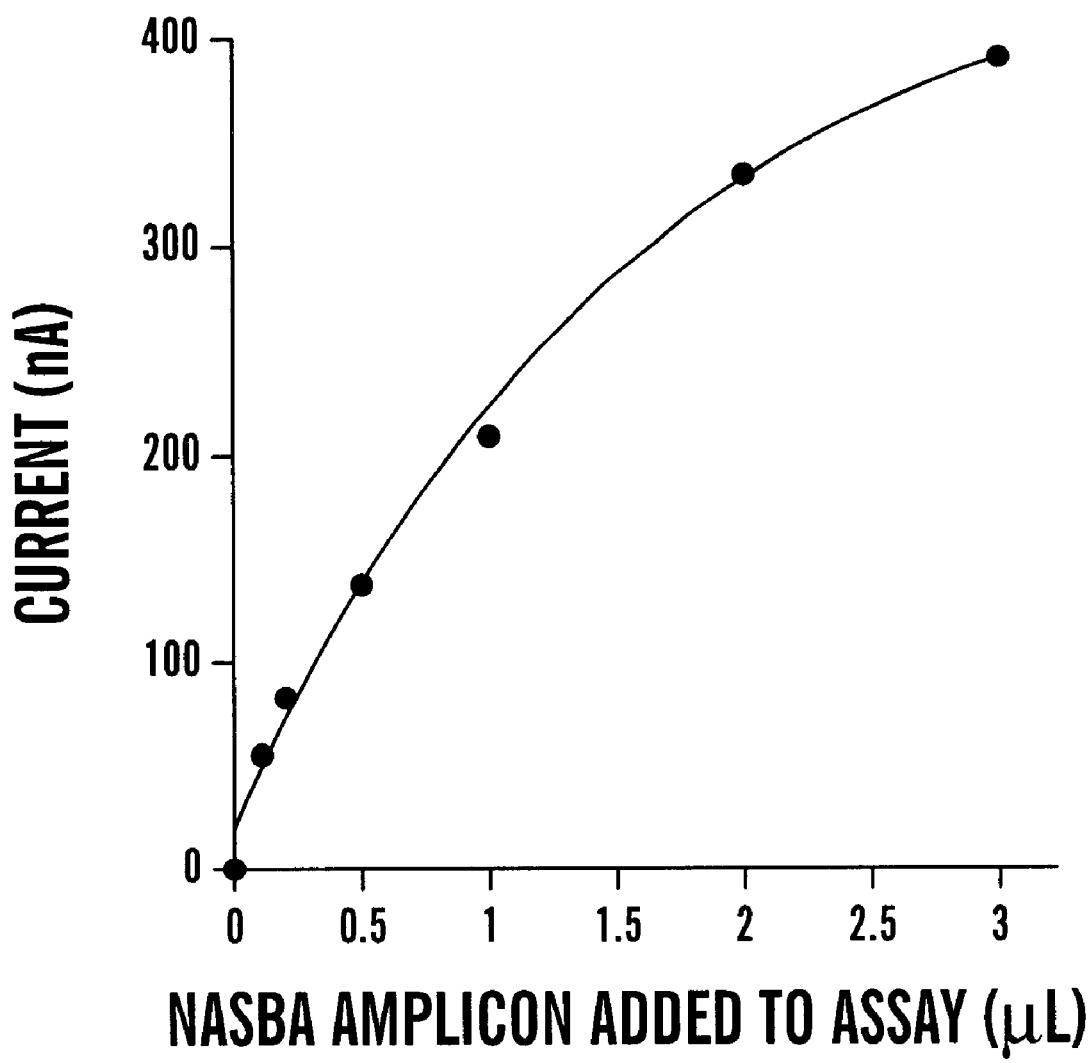
FIG. 12 is a graph of current generated versus volume of NASBA amplicon added to the assay.

Difference amounts of NASBA amplicon derived from the amplification of C. parvum oocyst mRNA were detected using a 3-pad assembly, as shown in FIG. 12. Background signals (derived from NASBA amplicons of $H_2O$) were subtracted.

Figure 10:
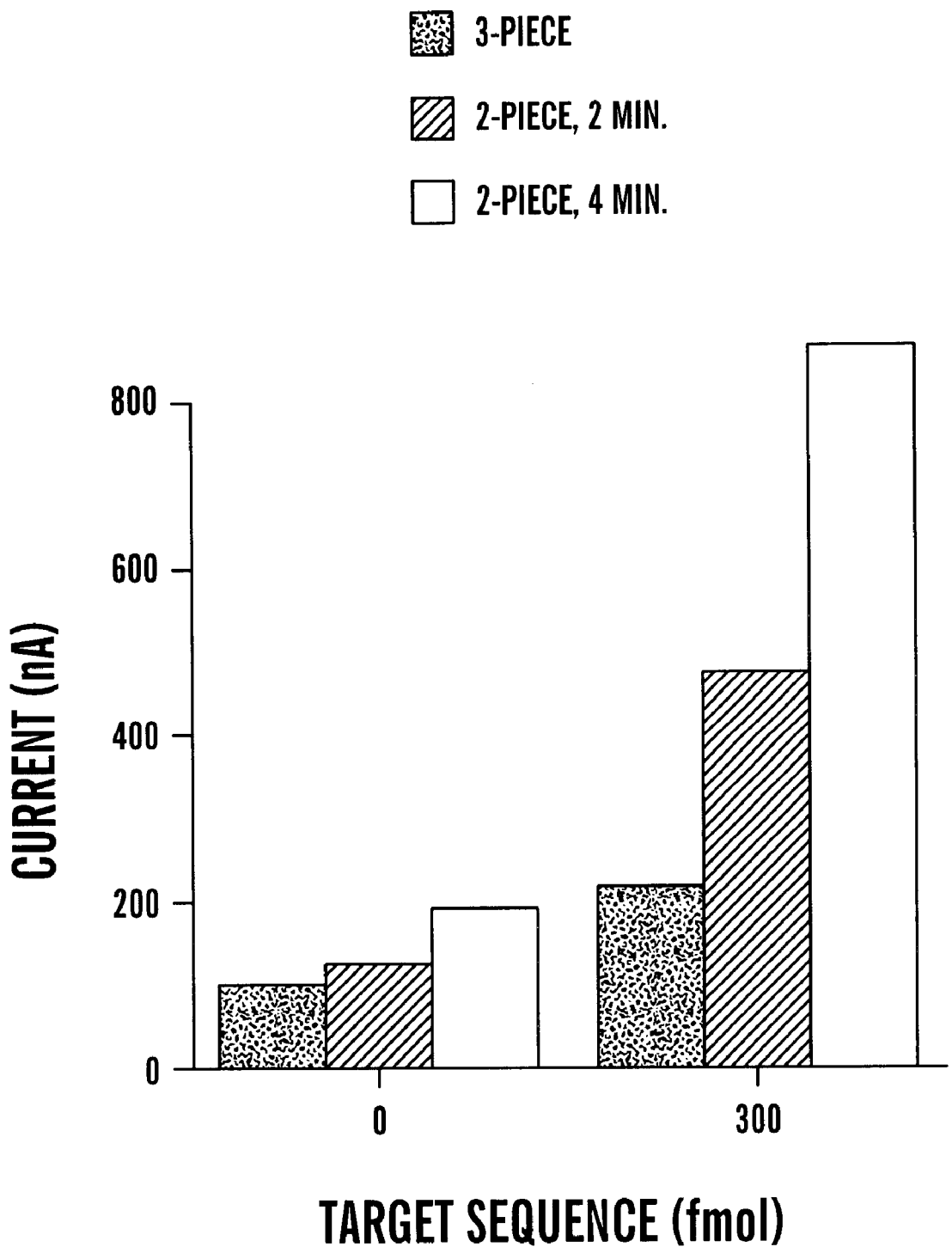
FIG. 10 is a graph of current generated versus synthetic target sequence concentration for two device configurations.

FIG. 10 shows the results of experiments used to design the test device. It shows the current generated from two concentrations (zero and 300 fmol) of synthetic target sequence using 2-pad and 3-pad assemblies. Using the 2-pad assembly, two different incubation times (2 min. and 4 min.) following introduction of the conjugate suspension directly onto the capture portion (and prior to the introduction of buffer solution to wash excess conjugate out of the capture portion) were investigated.

Figure 9:
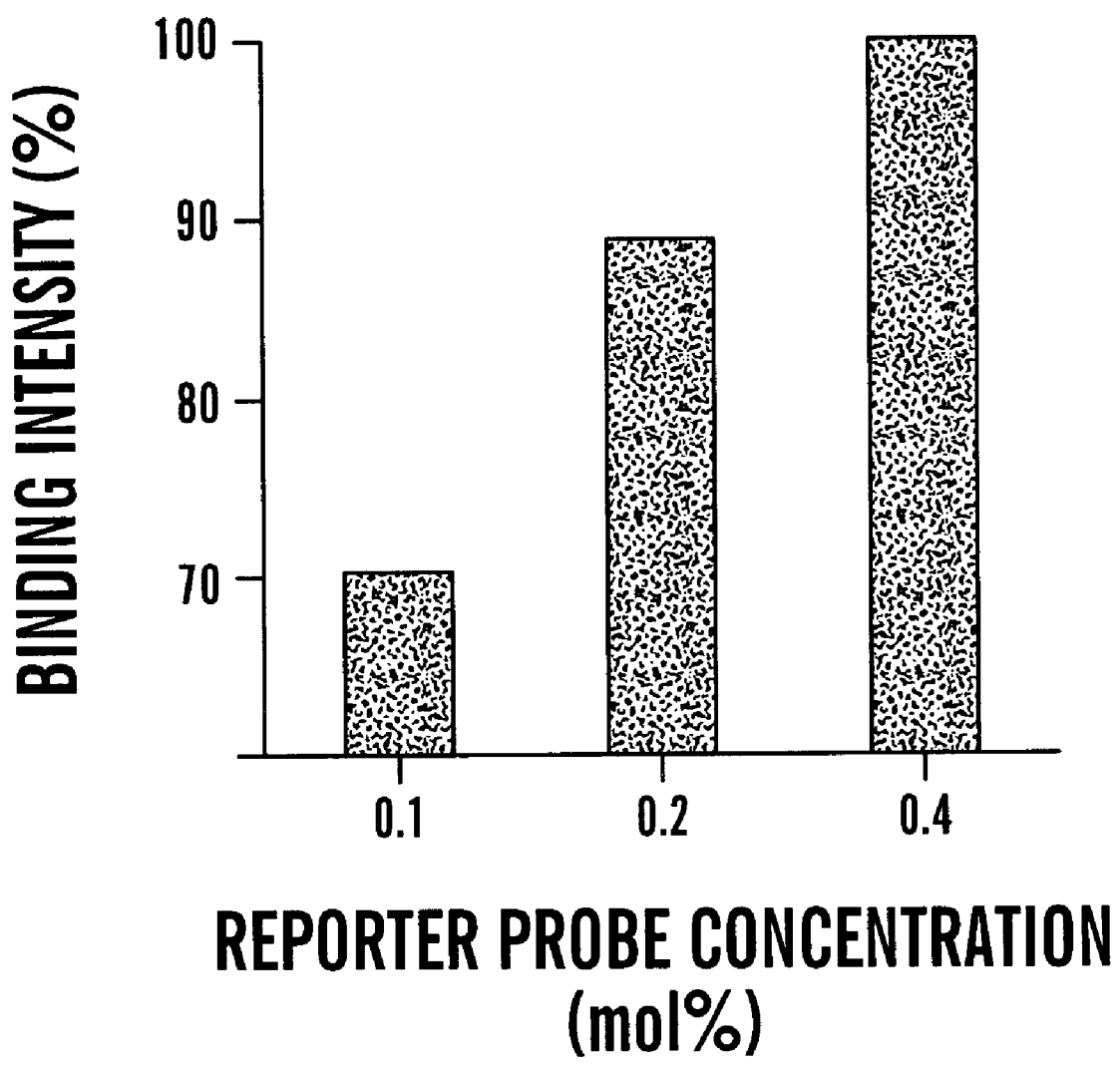
FIG. 9 is a graph of liposome-borne reporter probe/antisense reporter probe binding intensity versus reporter probe concentration.

FIG. 9 shows the results of an investigation of binding intensity for a reporter probe-antisense reporter probe pair at various concentrations of reporter probe on the liposome surface. The antisense reporter probe was immobilized on the capture portion of an absorbent pad. Optimization of the concentration of the second binding material on the liposomes requires consideration of a variety of factors. For example, a sufficient concentration of binding material must be employed to achieve good binding intensity, without sacrificing assay sensitivity. In addition, the concentration of the second binding material on the liposomes must be sufficient to accommodate the concentration of the analyte in the test sample, for example, to avoid the "hook effect" which could otherwise result from a high concentration of analyte.

A "dam" construction may alternatively be employed for signal detection. In this embodiment, the capture portion is not cut out of the strip for electrochemical detection; rather, the capture portion of the test strip is laid on top of the IDUA without isolating it from the remainder of the strip. However, any flow is stopped by blocking flow beyond the capture portion using a dam. Detergent is added Oust before the capture portion) and the signal is detected.

In order to validate the selections of primer and probe, different concentrations of the C. parvum hsp70 mRNA were used in a NASBA reaction, and the amplicons were detected using electrochemiluminescence (ECL) technology. The resulting data are presented in Table 4.

TABLE 4

Detection of hsp70 mRNA

| Number of molecules per NASBA reaction | Number of positives (total number = 6) | Average ECL value |
| --- | --- | --- |
| $5 \times 10^7$ | 6 | >2,000,000 |
| $5 \times 10^5$ | 6 | >2,000,000 |
| 5,000 | 6 | >2,000,000 |
| 500 | 6 | >2,000,000 |
| 50 | 6 | >2,000,000 |
| 25 | 5 | 1,900,000 |
| 10 | 6 | 1,600,000 |
| 0 | 0 | 400 |

A serial dilution of C. parvum oocysts was made in buffer solution. Nucleic acid was extracted out of the different samples (via Boom), amplified subsequently with NASBA and detected using electrochemiluminescence (ECL) technology. The resulting data are presented in Table 5.

TABLE 5

| No. of Oocysts per Sample (duplicates) | ECL Signal |
| --- | --- |
| 1,000,000 | positive |
| 100,000 | positive |
| 10,000 | positive |
| 1,000 | positive |
| 100 | positive |
| 10 | positive |
| 0 | negative |

The reliability of the data shown in Table 5 was verified using 10 replicates of two samples, as shown in Table 6.

TABLE 6

| No. of oocysts per sample | No. of replicates | Positives (%) |
| --- | --- | --- |
| 10 | 10 | 80 |
| 1 | 10 | 20 |

The disclosures of provisional U.S. application Serial No. 60/086,190, filed May 21, 1998, and provisional U.S. Serial No. 60/106,122, filed Oct. 29, 1998 are hereby incorporated by reference.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for detecting or quantifying an analyte in a liquid test sample, comprising:

providing a test device comprising:
  a contact portion on a first absorbent material;
  a capture portion either on said first absorbent material, or on a second absorbent material in fluid flow contact with said first absorbent material, wherein said capture portion has a first binding material bound to said capture portion; and
  an electrode array comprising a first conductor having a plurality of fingers, and a second conductor having a plurality of fingers, wherein said fingers of said first conductor are interdigitated with said fingers of said second conductor, said first and second conductors are electrically connected to one another via a voltage source and readout device, and said array is positioned to induce redox cycling of an electroactive marker released in said capture portion;
applying the test sample to said contact portion;
applying a voltage across said conductors, wherein said potential is sufficient to induce redox cycling of said marker;
allowing the test sample to migrate from said contact portion into said capture portion;
contacting the test sample with a liposome conjugate of liposomes and a second binding material, wherein said liposomes encapsulate an electroactive marker, wherein said second binding material binds with a portion of the analyte; and wherein said first binding material binds with a portion of the analyte other than the portion of the analyte for which the second binding material is selected;
incubating the test sample with the conjugate for a time sufficient to permit reaction between any analyte present in the test sample and the second binding material;
after said incubating and said allowing, lysing any liposomes present in said capture portion to release said marker, whereby said marker undergoes redox cycling induced by said conductors causing current to flow between said first and second conductors;
detecting the presence or amount of said current; and
correlating the presence or amount of said current with the presence or amount, respectively, of the analyte in the test sample.

2. A method for detecting or quantifying an analyte in a liquid test sample, comprising:
providing a test device comprising:
  a contact portion on a first absorbent material;
  a capture portion either on said first absorbent material, or on a second absorbent material in fluid flow contact with said first absorbent material, wherein said capture portion has a first binding material bound to said capture portion; and
  an electrode array comprising a first conductor having a plurality of fingers, and a second conductor having a plurality of fingers, wherein said fingers of said first conductor are interdigitated with said fingers of said second conductor, said first and second conductors are electrically connected to one another via a voltage source and readout device, and said array is positioned to induce redox cycling of an electroactive marker released from liposomes which migrate beyond said capture portion;
applying the test sample to said contact portion;
applying a voltage across said conductors, wherein said potential is sufficient to induce redox cycling of said marker;
allowing the test sample to migrate from said contact portion through said capture portion;
contacting the test sample with a liposome conjugate of liposomes and a second binding material, wherein said liposomes encapsulate an electroactive marker, wherein said second binding material binds with a portion of the analyte; and wherein said first binding material binds with a portion of the analyte other than the portion of said analyte for which said second binding material is selected;
incubating the test sample with the conjugate for a time sufficient to permit reaction between any analyte present in the test sample and the second binding material;
after said incubating and said allowing, lysing any liposomes which migrate beyond said capture portion to release said marker, whereby said marker undergoes redox cycling induced by said conductors causing current to flow between said first and second conductors;
detecting the presence or amount of said current; and
correlating the presence or amount of said current with the presence or amount, respectively, of the analyte in the test sample, wherein the presence or amount of said current is inversely proportional to the presence or amount, respectively, of the analyte in the test sample.

3. A method according to claim 1, wherein said contacting is carried out before said applying the test sample.

4. A method according to claim 1, wherein said contacting and said incubating are carried out before said applying the test sample.

5. A method according to claim 1, wherein said lysing is carried out by introducing a liposome lysing agent onto said capture portion after said allowing and said incubating.

6. A method according to claim 1, wherein said analyte is a target nucleic acid molecule, said first binding material is a capture probe selected to at least partially hybridize with a portion of said target nucleic acid molecule, and said second binding material is a reporter nucleic acid molecule selected to at least partially hybridize with a portion of said target nucleic acid molecule other than the portion of said target nucleic acid molecule for which said capture probe is selected.

7. A method according to claim 6, wherein said target nucleic acid molecule is found in an organism selected from the group consisting of bacteria, fungi, viruses, protozoa, and parasites.

8. A method according to claim 7, wherein said organism is *Cryptosporidium parvum*.

9. A method according to claim 1, further comprising introducing a wicking reagent to said first absorbent material after said applying of the test sample to carry the test sample into said capture portion.

10. A method according to claim 1, wherein said contacting is carried out by applying the test sample and the liposome conjugate to said absorbent material and allowing the test sample or the conjugate to migrate into contact with the other.

11. A method according to claim 1, wherein said contacting is carried out by reversibly immobilizing the liposome conjugate on said absorbent material between said contact portion and said capture portion, and allowing the test sample to migrate through the immobilized conjugate toward said capture portion.

12. A method according to claim 1, wherein said correlating is carried out by comparing the amount of the current flowing between the first and second conductors with one or more reference standards having known concentrations of the analyte for particular current amounts to determine the analyte concentration in the test sample relative to the known concentrations.

13. A method according to claim 1, wherein the liposomes are prepared from one or more phospholipids, glycolipids, steroids, alkyl phosphates, or fatty acid esters.

14. A method according to claim 1, wherein said fingers of said first conductor and said second conductor are each from about 1 µm to about 20 µm wide and are spaced from about 0.5 µm to about 10 µm apart.

15. A method according to claim 1, wherein said marker is selected from the group consisting of ferrocyanide, ferricyanide, and mixtures thereof.

16. A method according to claim 1, wherein said test device further comprises a third absorbent material in fluid flow contact with said second absorbent material and positioned to wick fluid from said second absorbent material.

17. A method according to claim 1, wherein at least one of said first and second absorbent materials has been treated with one or more blocking agents, surfactants, or mixtures thereof.

18. A method according to claim 17, wherein said blocking agents are selected from the group consisting of gelatin, non-fat dry milk, bovine serum albumin, keyhold limpet hemocyanin, and casein.

19. A method according to claim 1, further comprising isolating said capture portion from said first or second absorbent material after said allowing and before said detecting.

20. A test device for detecting or quantifying an analyte in a liquid test sample, said test device comprising:
   a contact portion on a first absorbent material;
   a capture portion either on said first absorbent material, or on a second absorbent material in fluid flow contact with said first absorbent material, wherein said capture portion has a binding material specific for the analyte bound to said capture portion; and
   an electrode array comprising a first conductor having a plurality of fingers, and a second conductor having a plurality of fingers, wherein said fingers of said first conductor are interdigitated with said fingers of said second conductor, and wherein said electrode array is positioned to induce redox cycling of an electroactive marker released in said capture portion.

21. A test device for detecting or quantifying an analyte in a liquid test sample, said test device comprising:
   a contact portion on a first absorbent material;
   a capture portion either on said first absorbent material, or on a second absorbent material in fluid flow contact with said first absorbent material, wherein said capture portion has a binding material specific for the analyte bound to said capture portion; and
   an electrode array comprising a first conductor having a plurality of fingers, and a second conductor having a plurality of fingers, wherein said fingers of said first conductor are interdigitated with said fingers of said second conductor, and wherein said electrode array is positioned to induce redox cycling of an electroactive marker released from liposomes which migrate out of said capture portion.

22. A test device according to claim 20, wherein said test device further comprises a reference electrode in electrical contact with said electrode array.

23. A test device according to claim 20, wherein either or both of said first conductor and said second conductor comprise one or more materials selected from the group consisting of platinum, gold, graphite, and silver.

24. A test device according to claim 20, wherein each of said first conductor and said second conductor comprise from 2 to 1000 fingers.

25. A test device according to claim 20, wherein said fingers of said first conductor and said second conductor are each from about 1 µm to about 20 µm wide and are spaced from about 0.5 µm to about 10 µm apart.

26. A test device according to claim 20, wherein said fingers of said first conductor and second conductor are at least partially coated with an insulating material.

27. A test device according to claim 20, wherein said test device further comprises a third absorbent material in fluid flow contact with said second absorbent material and positioned to wick fluid from said second absorbent material.

28. A test device according to claim 20, wherein said test device further comprises a support on which at least one of said first absorbent material or said second absorbent material is mounted.

* * * * *